United States Patent
Bacilieri et al.

(10) Patent No.: US 12,071,406 B2
(45) Date of Patent: Aug. 27, 2024

(54) CRYSTALLINE FORMS OF AN NK-1 ANTAGONIST

(71) Applicant: Helsinn Healthcare SA, Pazallo-Lugano (CH)

(72) Inventors: Christian Bacilieri, Breganzona (CH); Gionata Frasca, Minusio (CH)

(73) Assignee: Helsinn Healthcare SA, Pazzallo (CH)

( * ) Notice: Subject to any disclaimer, the term of this patent is extended or adjusted under 35 U.S.C. 154(b) by 729 days.

(21) Appl. No.: 17/185,206

(22) Filed: Feb. 25, 2021

(65) Prior Publication Data

US 2021/0269401 A1   Sep. 2, 2021

Related U.S. Application Data

(63) Continuation of application No. 16/863,038, filed on Apr. 30, 2020, now Pat. No. 10,961,195, which is a continuation of application No. 16/259,913, filed on Jan. 28, 2019, now Pat. No. 10,676,440, which is a continuation of application No. 15/918,868, filed on Mar. 12, 2018, now Pat. No. 10,233,154, which is a continuation of application No. 14/865,370, filed on Sep. 25, 2015, now Pat. No. 9,951,016.

(60) Provisional application No. 62/055,836, filed on Sep. 26, 2014.

(51) Int. Cl.
    *C07D 213/75* (2006.01)
(52) U.S. Cl.
    CPC .................. *C07D 213/75* (2013.01)
(58) Field of Classification Search
    CPC ....... C07D 213/75; C07D 401/04; A61P 1/08; A61P 25/00; A61P 35/00; A61P 43/00; C07B 2200/13; A61K 31/444; A61K 31/496
    See application file for complete search history.

(56) References Cited

U.S. PATENT DOCUMENTS

| | | |
|---|---|---|
| 5,021,242 A | 6/1991 | Romer |
| 5,271,944 A | 12/1993 | Lee |
| 5,922,355 A | 7/1999 | Parikh |
| 6,297,375 B1 | 2/2001 | Boes et al. |
| 6,994,283 B1 | 2/2006 | Yuki |
| 7,655,800 B2 | 2/2010 | Chase |
| 9,951,016 B2 | 4/2018 | Bacilieri |
| 10,233,154 B2 | 3/2019 | Bacilieri |
| 10,676,440 B2 | 6/2020 | Bacilieri |
| 2002/0091265 A1* | 7/2002 | Bos ................ A61P 19/02 546/276.4 |
| 2013/0143897 A1 | 6/2013 | Bhutada |
| 2013/0245069 A1 | 9/2013 | Jacobsen |

FOREIGN PATENT DOCUMENTS

DE    100 08 042 A1    8/2000

OTHER PUBLICATIONS

Hancock et al. Polyamorphism: a pharmaceutical science perspective, Journal of Pharmacy or Pharmacology, 54, 1151-1152. (Year: 2002).*

Written Opinion and International Search Report, dated Apr. 22, 2016, which issued during the prosecution of International Patent Application No. PCT/IB/2015/002031, which corresponds to the present application.

T. Spinelli et al.. "Netupitant PET Imaging and ADME Studies in Humans", The Journal of Clinical Pharmacology, vol. 54 No. 1, Nov. 8, 2013.

Helsinn Chemicals S.A. Information guide, 1 page, retrieved from the Internet at http://www.chemeurope.com/en.companies/18420/helsinn-chemicals-s-a.html Jun. 24, 2017.

* cited by examiner

*Primary Examiner* — Matthew P Coughlin
*Assistant Examiner* — Meghan C Heasley
(74) *Attorney, Agent, or Firm* — Clark G. Sullivan

(57) ABSTRACT

The present invention is related to crystalline forms of 2-(3,5-bis(trifluoromethyl)phenyl)-N,2-dimethyl-N-(6-(4-methylpiperazin-1-yl)-4-(o-tolyl)pyridin-3-yl)propanamide which is an NK-1 antagonist useful in the treatment of induced vomiting and other disorders.

6 Claims, 17 Drawing Sheets

CRYSTALLINE FORMS OF AN NK-1 ANTAGONIST

FIELD OF THE INVENTION

The present invention is related to crystalline forms of 2-(3,5-bis(trifluoromethyl)phenyl)-N,2-dimethyl-N-(6-(4-methylpiperazin-1-yl)-4-(o-tolyl)pyridin-3-yl)propanamide which is an NK-1 antagonist useful in the treatment of induced vomiting and other disorders.

BACKGROUND OF THE INVENTION

The compound 2-(3,5-bis(trifluoromethyl)phenyl)-N,2-dimethyl-N-(6-(4-methylpiperazin-1-yl)-4-(o-tolyl)pyridin-3-yl)propanamide having Formula I.

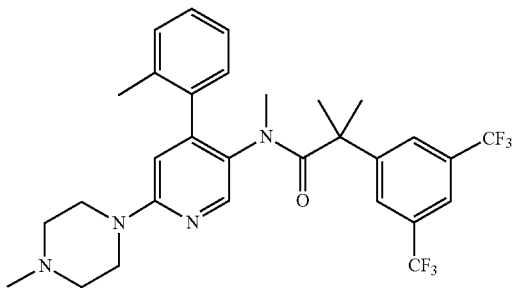

I is an antagonist of NK-1 useful in the treatment of various disorders including motion sickness and induced vomiting. The compound of Formula I, as well as its preparation and use, have been described in U.S. Pat. No. 6,297,375, which is incorporated herein by reference in its entirety.

For the development of a drug, it is typically advantageous to employ a form of the drug having desirable properties with respect to its preparation, purification, reproducibility, stability, bioavailability, and other characteristics. U.S. Pat. No. 6,297,375 discloses a solid free base form of the compound of Formula I in Example 14 (g) which is isolated by flash chromatography to yield the compound as "white crystals" with a melting point of 155-157° C. The example does not report the crystalline peaks for this free base. The example also does not report whether this crystalline form of the free base was solvated or hydrated. The compound was subsequently crystallized as the HCl salt. Accordingly, the crystalline forms of the compound of Formula I provided herein help satisfy the ongoing need for the development of NK-1 antagonists for the treatment of serious diseases and disorders.

SUMMARY OF THE INVENTION

The present invention provides a crystalline form of the compound of Formula I.

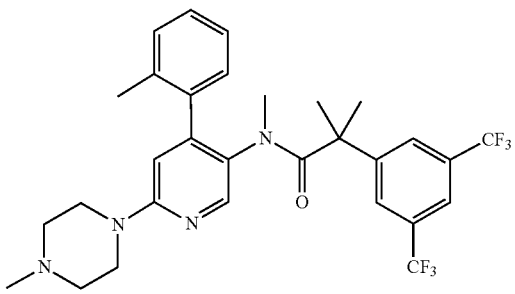

I which is any one of Forms I, II, and III described herein.

The present invention further provides a crystalline form of the compound of Formula I which is which is non-solvated.

The present invention further provides a crystalline form of the compound of Formula I which is a trifluoroethanol solvate.

The present invention further provides a crystalline form of the compound of Formula I which is a formate salt.

The present invention further provides a composition comprising a crystalline form of the invention and at least one pharmaceutically acceptable carrier.

The present invention further provides a process for preparing a crystalline form of the invention.

The present invention further provides a method of treating a disease associated with activity of NK-1 receptor in a patient, comprising administering to the patient a therapeutically effective amount of a crystalline form of the invention.

DETAILED DESCRIPTION

Figure 1:
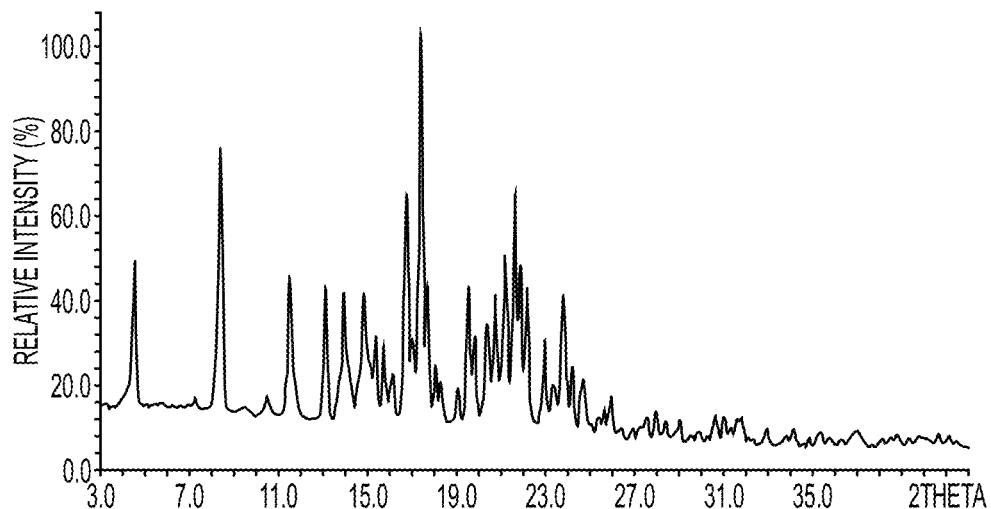
FIG. 1 shows an XRPD pattern for Form I.

The present invention relates to, inter alia, crystalline forms of the NK-1 receptor antagonist 2-(3,5-bis(trifluoromethyl)phenyl)-N,2-dimethyl-N-(6-(4-methylpiperazin-1-yl)-4-(o-tolyl)pyridin-3-yl)propanamide having Formula I.

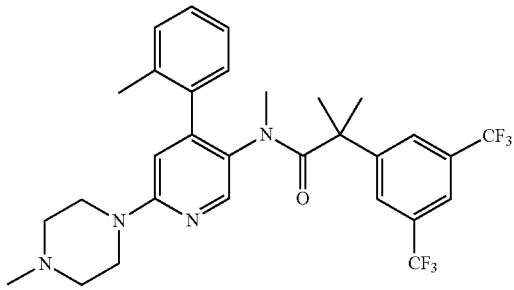

I which are useful, for example, in the preparation of solid dosage forms of the above compound for the treatment of various diseases, including cancer.

Typically, different crystalline forms of the same substance have different bulk properties related to, for example, hygroscopicity, solubility, stability, and the like. Forms with high melting points often have good thermodynamic stability which is advantageous in prolonging shelf-life of drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-Ray Powder Diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichimetric, where the water content is variable and dependent on external conditions such as humidity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2θ values. Thus, peak assignments, such as those reported herein, can vary by plus or minus about 0.2° (2θ), and the term "substantially" as used in the context of XRPD herein is meant to encompass the above-mentioned variations.

In the same way, temperature readings in connection with DSC, TGA, or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. Accordingly, a crystalline form reported herein having a DSC thermogram "substantially" as shown in any of the Figures is understood to accommodate such variation.

The compound of Formula I can be isolated in numerous crystalline forms, including crystalline forms which are anhydrous, hydrated, non-solvated, or solvated. Example hydrates include hemihydrates, monohydrates, dihydrates, and the like. In some embodiments, the crystalline form of the compound of Formula I is anhydrous and non-solvated. By "anhydrous" is meant that the crystalline form of the compound of Formula I contains essentially no bound water in the crystal lattice structure, i.e., the compound does not form a crystalline hydrate.

The compound of Formula I can also be isolated as a clathrate such that the stoichiometry of water to the compound of Formula I in the crystalline lattice can vary without impacting the crystalline structure of the molecule. The degree of hydration (i.e. stoichiometirc ratio of water to compound of Formula I) can range from greater than zero to as much as 3 without changing the crystalline form of the molecule. In some embodiments, the compound of Formula I has a degree of hydration of from 0.5 to 2.5. In other embodiments, the crystalline form of the compound of Formula I has a degree of hydration of from 1.0 to 2.0. Moreover, in any of these embodiments, the crystalline clathrate can further include an organic volatile impurity without impacting the crystalline structure of the molecule, such as methanol, ethanol, or isopropanol.

The compound of Formula I can also be isolated in crystalline salt forms. Crystalline salt forms of the invention can be prepared by any suitable method for the preparation of acid addition salts. For example, the free base of the compound of Formula I can be combined with the desired acid in a solvent or in a melt. Alternatively, an acid addition salt of Formula I can be converted to a different acid addition salt by anion exchange. Crystalline salts of the invention which are prepared in a solvent system can be isolated by precipitation from the solvent. Precipitation and/or crystallization can be induced, for example, by evaporation, reduction of temperature, addition of anti-solvent, or combinations thereof.

In some embodiments, the crystalline forms of the invention are substantially isolated. By "substantially isolated" is meant that a particular crystalline form of the compound of Formula I is at least partially isolated from impurities. For example, in some embodiments, a crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances.

In some embodiments, a crystalline form of the compound of Formula I is substantially free of other crystalline forms. The phrase "substantially free of other crystalline forms" means that a particular crystalline form of the compound of Formula I comprises greater than about 80%, greater than about 90%, greater than about 95%, greater than about 98%, greater than about 99%, or greater than about 99.5% by weight of the particular crystalline form.

In some embodiments, particularly the Crystalline Form I embodiments, the compound is present as a micronized compound. It has surprisingly been discovered that netupitant free base is well-absorbed when present as Crystalline Form I, even superior to certain salts, and that this absorption can be improved even further by micronizing the compound. In one embodiment, at least 90% of the particles are greater than 0.01 or 0.1 microns and less than 500, 100, 50 or 10 microns.

Crystalline Form I

In some embodiments, the crystalline form of the compound of Formula I is Form I. Form I is an anhydrous and non-solvated crystalline form of the compound of Formula I. This crystalline form can be generally prepared by combining the compound 2-(3,5-bis(trifluoromethyl)phenyl)-N,2-dimethyl-N-(6-(4-methylpiperazin-1-yl)-4-(o-tolyl)pyridin-3-yl)propanamide with a solution of toluene and n-heptane and heating the resulting mixture.

In some embodiments, the process for preparing crystalline Form I comprises:

combining the compound 2-(3,5-bis(trifluoromethyl)phenyl)-N,2-dimethyl-N-(6-(4-methylpiperazin-1-yl)-4-(o-tolyl)pyridin-3-yl)propanamide with a solution of toluene and n-heptane;

heating the mixture resulting from the combining of the compound and solution;

filtering the heated mixture;

cooling the filtered mixture to afford a crystalline solid; and isolating the crystalline solid.

In some embodiments, the heating step is performed at reflux temperature.

In some embodiments, the cooling step is performed at a temperature of −10° C.

In some embodiments, the cooling step is performed for one hour at −10° C.

Crystalline Form I can be identified by unique signatures with respect to, for example, X-ray powder diffraction (XRPD), differential scanning calorimetry (DSC), thermogravimetric analysis (TGA), and dynamic vapor sorption (DVS). In some embodiments, crystalline Form I is characterized by an XRPD pattern substantially as shown in FIG. 1. Peaks from the XRPD pattern are listed in Table 1.

Figure 23:
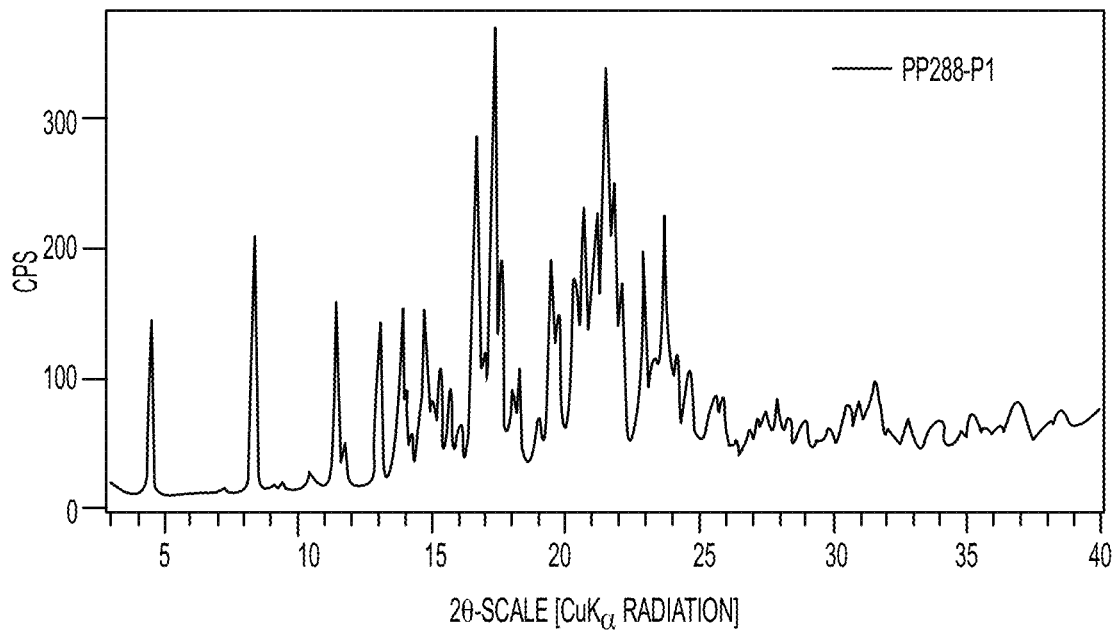
FIG. 23 shows an XRPD pattern for Form I.

In some embodiments, crystalline Form I is characterized by an XRPD pattern substantially as shown in FIG. 23. Peaks from the XRPD pattern are listed in Table 9.

In some embodiments, crystalline Form I is characterized by an XRPD pattern comprising a peak, in terms of 2θ, at 4.5° 0.2°. In some embodiments, crystalline Form I has an XRP pattern comprising the following peaks, in terms of 2θ: 4.5°±0.2°; 8.4°±0.2°; 11.5°±0.2°; 13.1°±0.2°; 13.9°±0.2°; 14.8°±0.2°; 16.7°±0.2°; 17.4°±0.2°; 17.7°±0.2°; 19.5°±0.2°; 21.2°±0.2°; 21.6°±0.2°; 21.8°±0.2°. In some embodiments, crystalline Form I has an XRPD pattern comprising 2, or more, 3 or more, or 4 or more of the following peaks, in terms of 2θ: 4.5°±0.2°; 8.4°±0.2°; 11.5°±0.2°; 13.1°±0.2°; 13.9°±0.2°; 14.8°±0.2°; 16.7°±0.2°; 17.4°±0.2°; 17.7°±0.2°; 19.5°±0.2°; 21.2°±0.2°; 21.6°±0.2°; 21.8°±0.2°.

Figure 2:
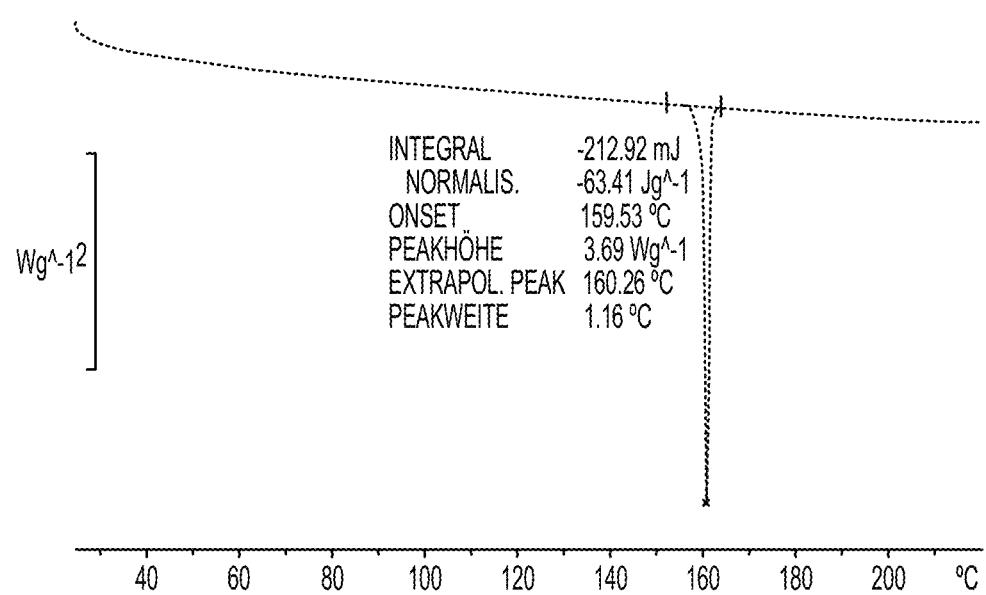
FIG. 2 shows the results of a DSC experiment for Form I.

In some embodiments, Form I is characterized by a DSC thermogram comprising an endothermic peak having a maximum at about 160.3° C. In some embodiments, crystalline Form I has a DSC thermogram substantially as shown in FIG. 2.

Figure 3:
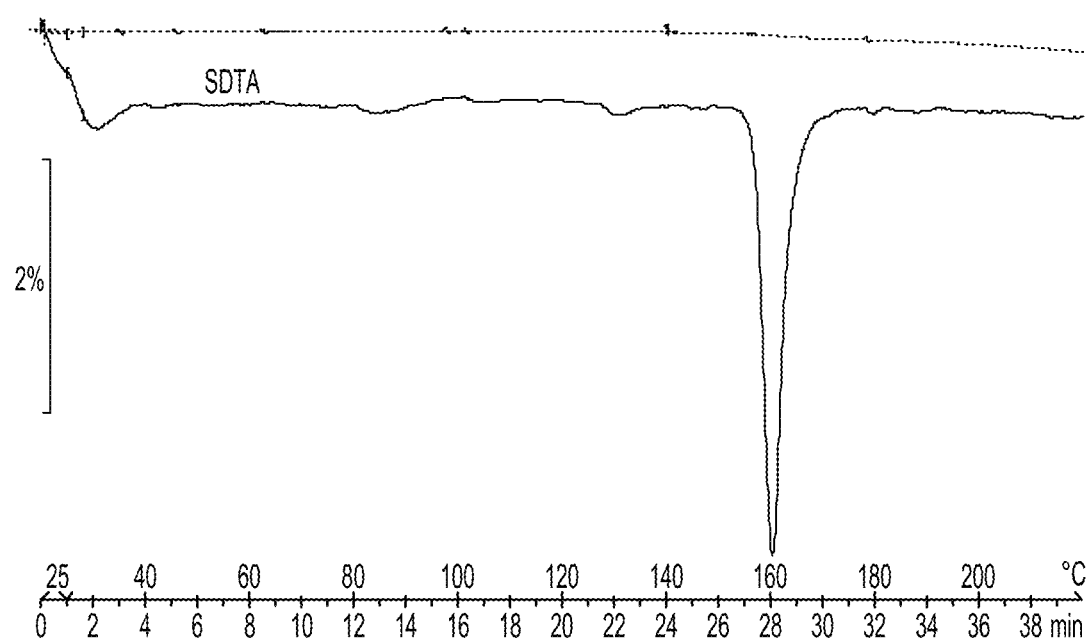
FIG. 3 shows the results of a TGA experiment for Form I.

In some embodiments, crystalline Form I has a TGA trace substantially as shown in FIG. 3.

Figure 4:
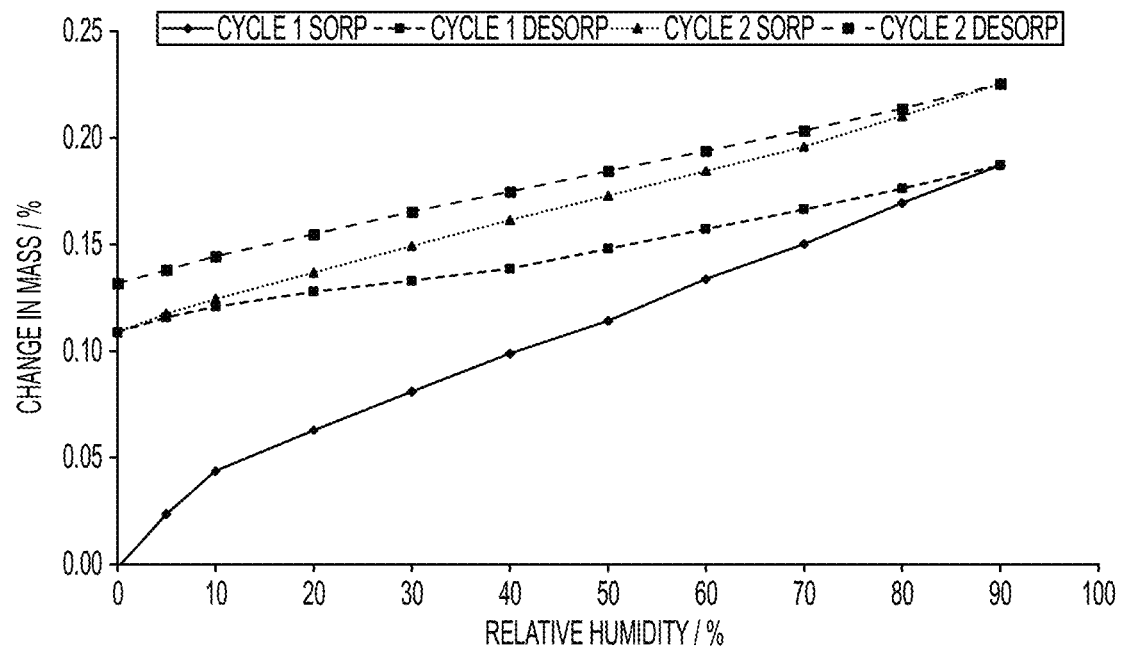
FIG. 4 shows the results of a DVS experiment for Form I.

In some embodiments, crystalline Form I has a DVS trace substantially as shown in FIG. 4.

Figure 9:
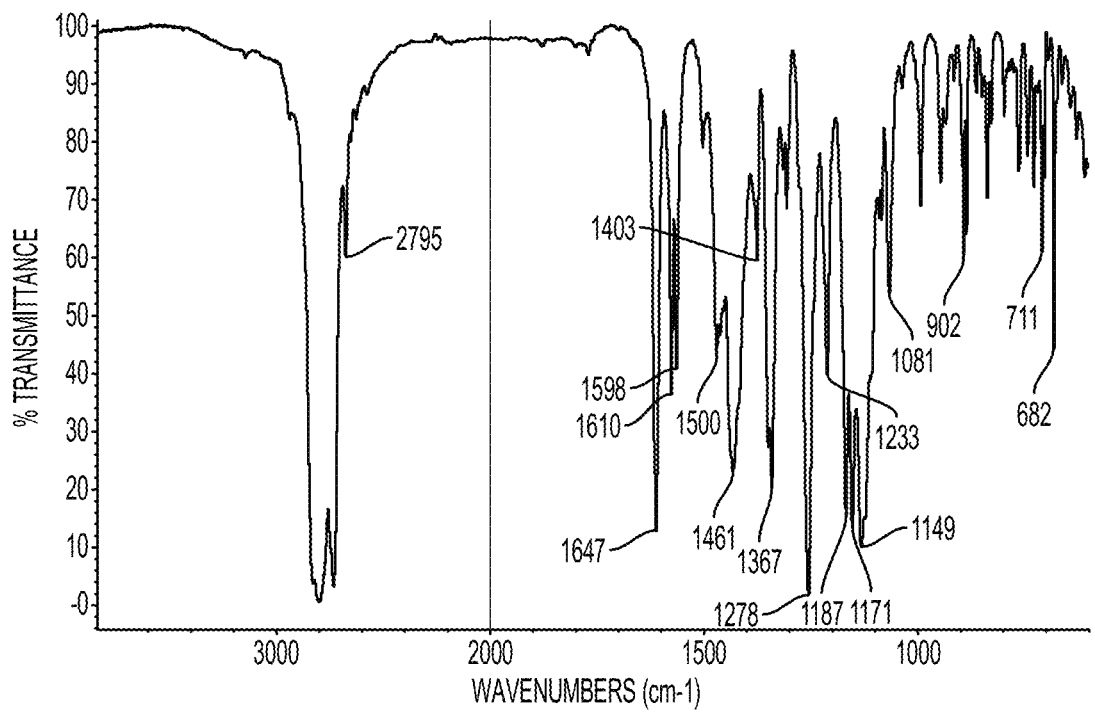
FIG. 9 shows an IR spectrum for Form I.

In some embodiments, crystalline Form I has an IR spectrum substantially as shown in FIG. 9.

Figure 10:
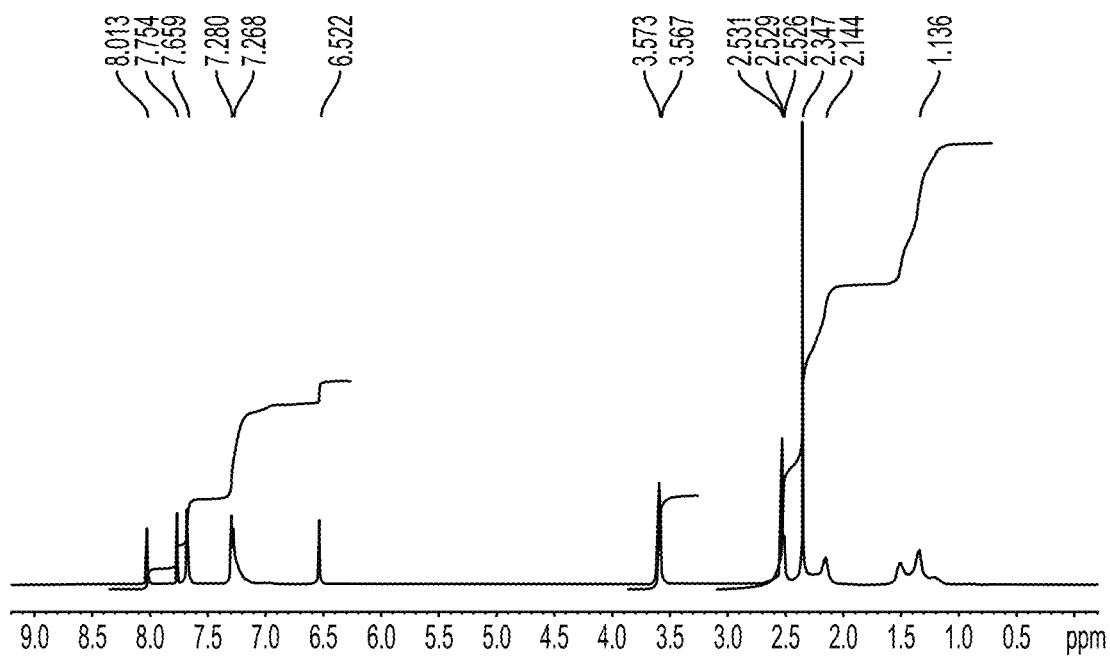
FIG. 10 shows an NMR spectrum for Form I.

In some embodiments, crystalline Form I has an NMR spectrum substantially as shown in FIG. 10.

Figure 25:
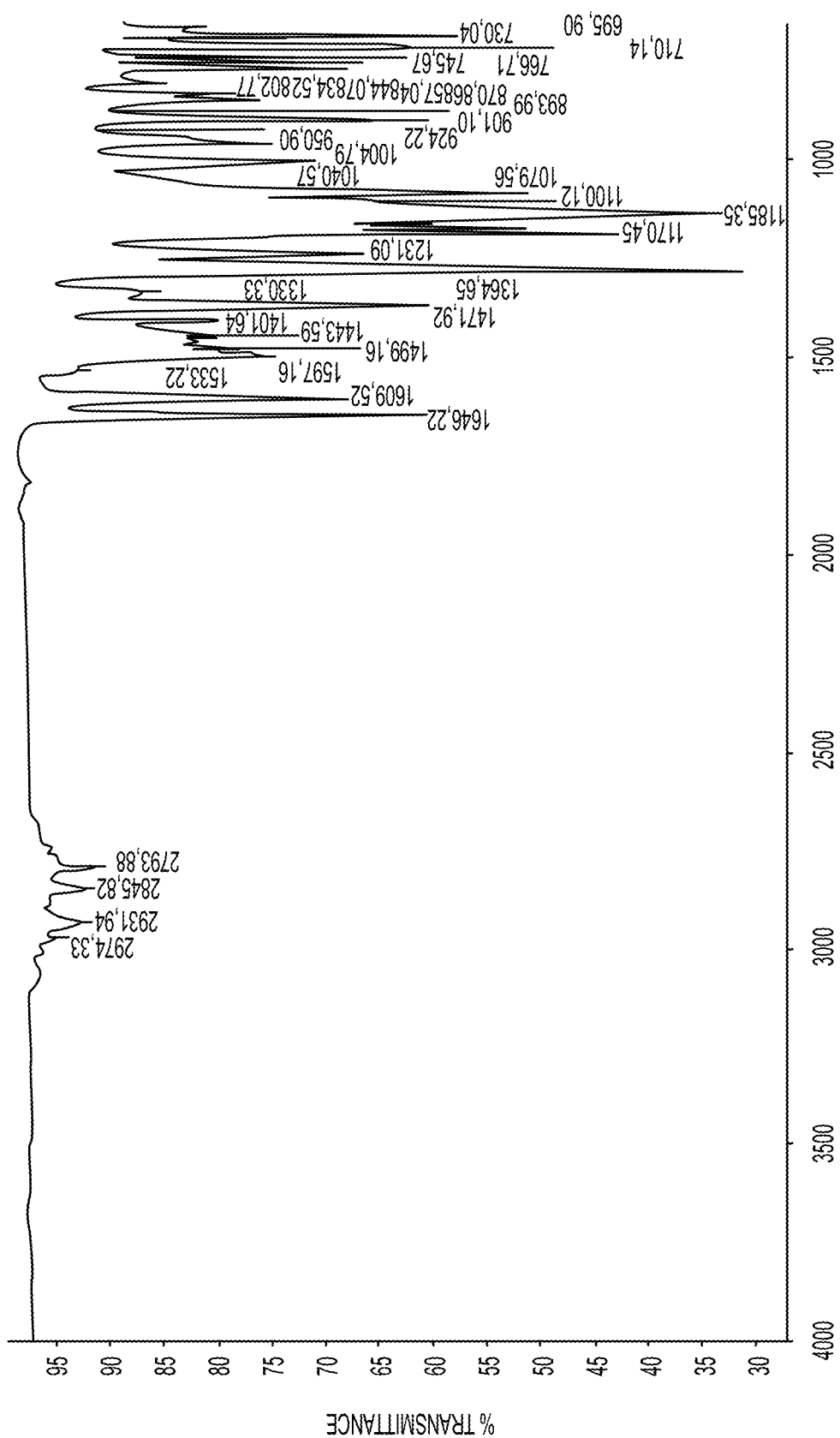
FIG. 25 shows an FT-IR spectrum for Form I.

In some embodiments, crystalline Form I has an FT-IR spectrum substantially as shown in FIG. 25

Figure 24:
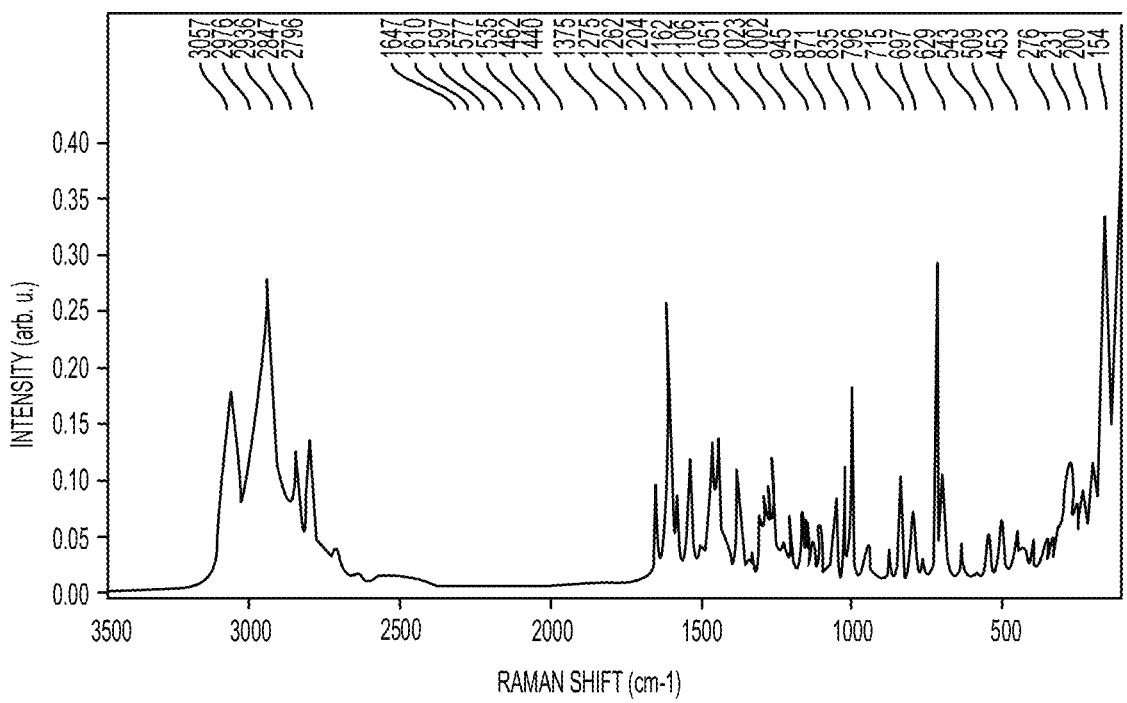
FIG. 24 shows an FT-Raman spectrum for Form I.

In some embodiments, crystalline Form I has an FT-Raman trace substantially as shown in FIG. 24.

Crystalline Form II

In some embodiments, the crystalline form of the compound of Formula I is Form II. Form II is a crystalline trifluoroethanol solvate of the compound of Formula I. This crystalline form can be generally prepared by combining the compound 2-(3,5-bis(trifluoromethyl)phenyl)-N,2-dimethyl-N-(6-(4-methylpiperazin-1-yl)-4-(o-tolyl)pyridin-3-yl)propanamide with a solution of trifluoroethanol and water and heating the resulting mixture.

In some embodiments, the process for preparing crystalline Form II comprises:

combining the compound 2-(3,5-bis(trifluoromethyl)phenyl)-N,2-dimethyl-N-(6-(4-methylpiperazin-1-yl)-4-(o-tolyl)pyridin-3-yl)propanamide with a solution of trifluoroethanol and water;

heating the mixture resulting from the combining of the compound and solution;

filtering the heated mixture;

cooling the filtered mixture to afford a crystalline solid; and isolating the crystalline solid.

In some embodiments, the heating step is performed at a temperature of 70° C.

In some embodiments, the cooling step is performed at a temperature of 3° C.

Figure 17:
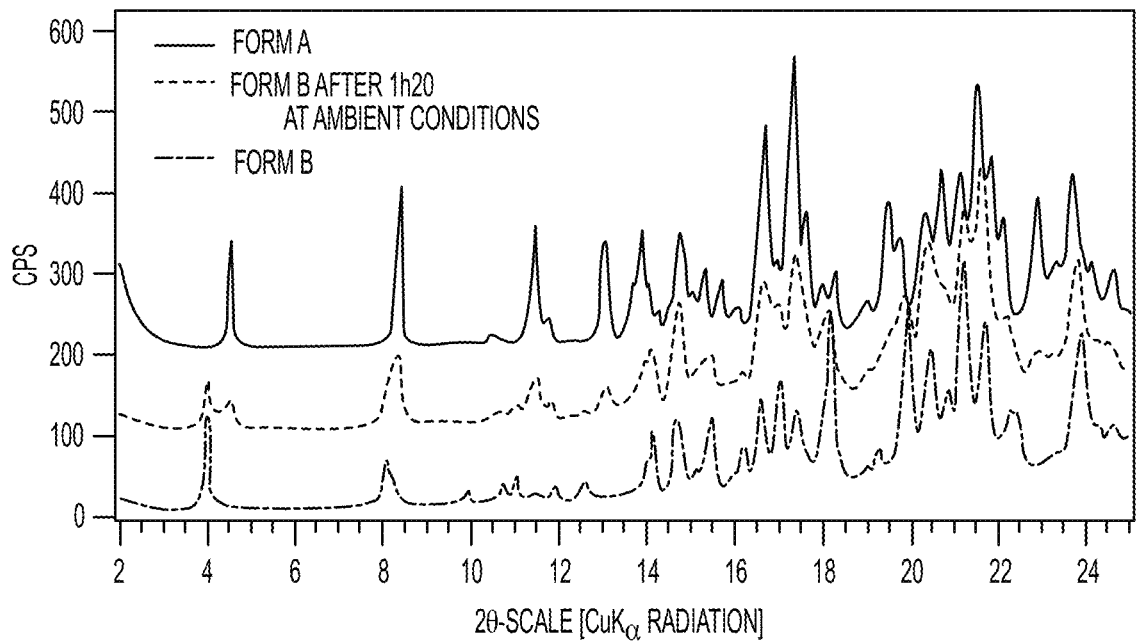
FIG. 17 shows an XRPD pattern for Form II.

Crystalline Form II can be identified by unique signatures with respect to, for example, XRPD, DSC, TGA, and DVS. In some embodiments, crystalline Form II is characterized by an XRPD pattern substantially as shown in FIG. 17. Peaks from the XRPD pattern are listed in Table 7.

In some embodiments, crystalline Form II is characterized by an XRPD pattern comprising a peak, in terms of 2θ, at 4.0°±0.2°. In some embodiments, crystalline Form II has an XRPD pattern comprising the following peaks, in terms of 2θ: 4.0°±0.2°; 14.7°±0.2°; 15.5°±0.2°; 16.6°±0.2°; 17.0°±0.2°; 17.4°±0.2°; 18.2°±0.2°; 19.9°±0.2°; 20.4°±0.2°; 20.8°±0.2°; 21.2°±0.2°; 21.7°±0.2°; and 23.9°±0.2°. In some embodiments, crystalline Form II has an XRPD pattern comprising 2, or more, 3 or more, or 4 or more of the following peaks, in terms of 2θ: 4.0°±0.2°; 14.7°±0.2°; 15.5°±0.2°; 16.6°±0.2°; 17.0°±0.2°; 17.4°±0.2°; 18.2°±0.2°; 19.9°±0.2°; 20.4°±0.2°; 20.8°±0.2°; 21.2°±0.2°; 21.7°±0.2°; and 23.9°±0.2°. In some embodiments, crystalline Form II has an XRPD pattern comprising the following peaks, in terms of 2θ: 4.0°±0.2°; 15.5°±0.2°; 17.0°±0.2°; 18.2°±0.2°; 19.9±0.2°; 20.4°±0.2°; and 23.9°±0.2°.

Figure 18:
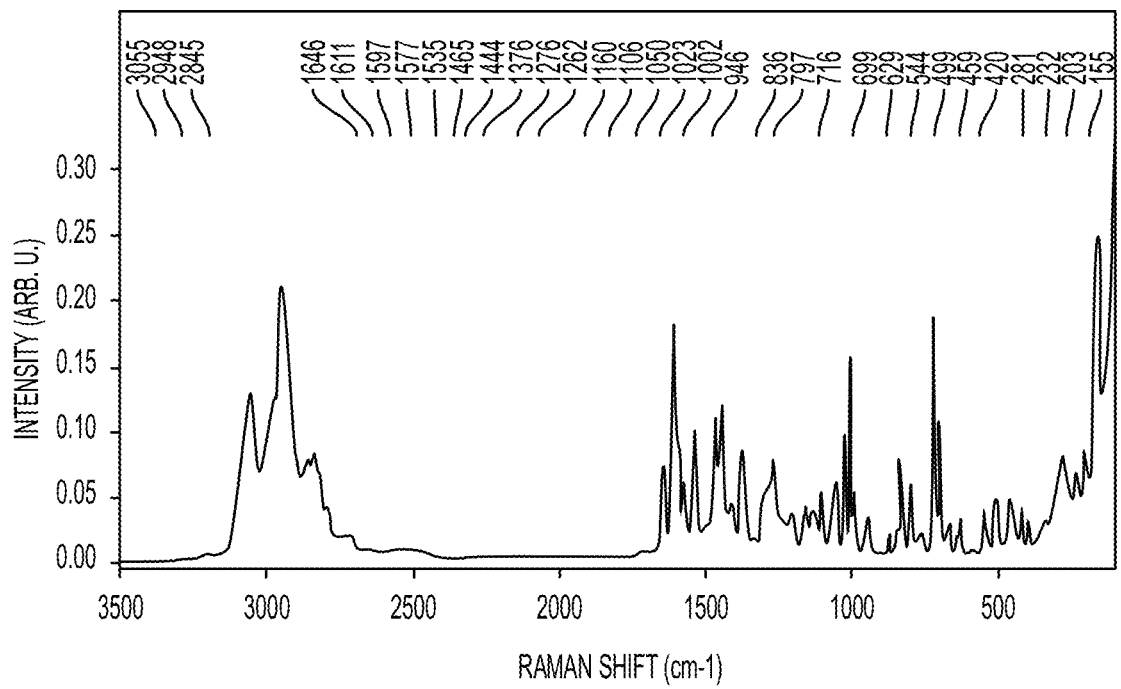
FIG. 18 shows an FT-Raman spectrum for Form II.

In some embodiments, crystalline Form II has an FT-Raman trace substantially as shown in FIG. 18.

Figure 19:
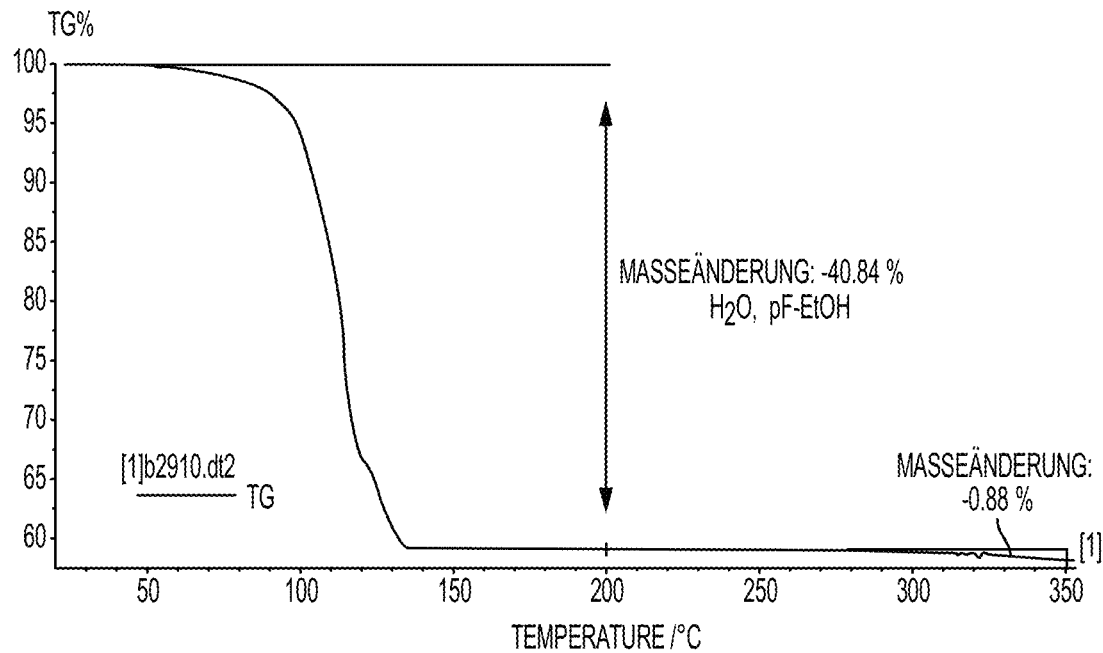
FIG. 19 shows the results of a TGA experiment for Form II.

In some embodiments, crystalline Form II has a TGA trace substantially as shown in FIG. 19.

Crystalline Form III

In some embodiments, the crystalline form of the compound of Formula I is Form III. Form III is a crystalline formate salt of the compound of Formula I. This crystalline form can be generally prepared by combining the compound 2-(3,5-bis(trifluoromethyl)phenyl)-N,2-dimethyl-N-(6-(4-methylpiperazin-1-yl)-4-(o-tolyl)pyridin-3-yl)propanamide with a solution of formic acid and water.

In some embodiments, the process for preparing crystalline Form II comprises:

combining the compound 2-(3,5-bis(trifluoromethyl)phenyl)-N,2-dimethyl-N-(6-(4-methylpiperazin-1-yl)-4-(o-tolyl)pyridin-3-yl)propanamide with a solution of formic acid and water;

heating the mixture resulting from the combining of the compound and solution;

filtering the heated mixture;

cooling the filtered mixture to afford a crystalline solid; and isolating the crystalline solid.

In some embodiments, the heating step is performed at a temperature of 23° C.

In some embodiments, the cooling step is performed at a temperature of 4° C.

Figure 20:
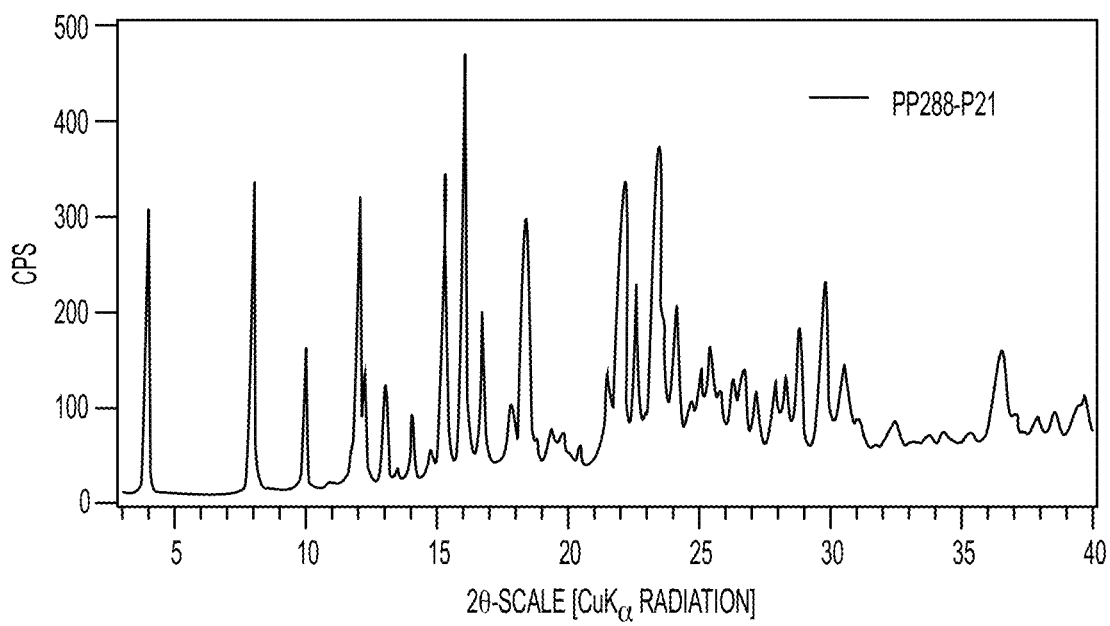
FIG. 20 shows an XRPD pattern for Form III.

Crystalline Form III can be identified by unique signatures with respect to, for example, XRPD, DSC, TGA, and DVS. In some embodiments, crystalline Form III is characterized by an XRPD pattern substantially as shown in FIG. 20. Peaks from the XRPD pattern are listed in Table 8.

In some embodiments, crystalline Form III is characterized by an XRPD pattern comprising a peak, in terms of 2θ, at 8.0°±0.2°. In some embodiments, crystalline Form III has an XRPD pattern comprising the following peaks, in terms of 2θ: 4.0°±0.2°; 8.0°±0.2°; 10.0°±0.2°; 12.0°±0.2°; 15.3°±0.2°; 16.0°±0.2°; 16.7°±0.2°; 18.4°±0.2°; 21.9°±0.2°; 22.10±0.2°; 23.3°±0.2°; 23.4°±0.2°; 23.6°±0.2°; and 24.1°±0.2°. In some embodiments, crystalline Form III has an XRPD pattern comprising 2, or more, 3 or more, or 4 or more of the following peaks, in terms of 2θ: 4.0°±0.2°; 8.0°±0.2°; 10.0°±0.2°; 12.0°±0.2°; 15.3°±0.2°; 16.0°±0.2°; 16.7°±0.2°; 18.4°±0.2°; 21.9°±0.2°; 22.1°±0.2°; 23.3°±0.2°; 23.4°±0.2°; 23.6°±0.2°; and 24.2°±0.2°. In some embodiments, crystalline Form III has an XRPD pattern comprising the following peaks, in terms of 2θ: 8.0°±0.2°; 10.0°±0.2°; 12.0°±0.2°; 16.0°±0.2°; 18.4°±0.2° and 23.4°±0.2°.

Figure 21:
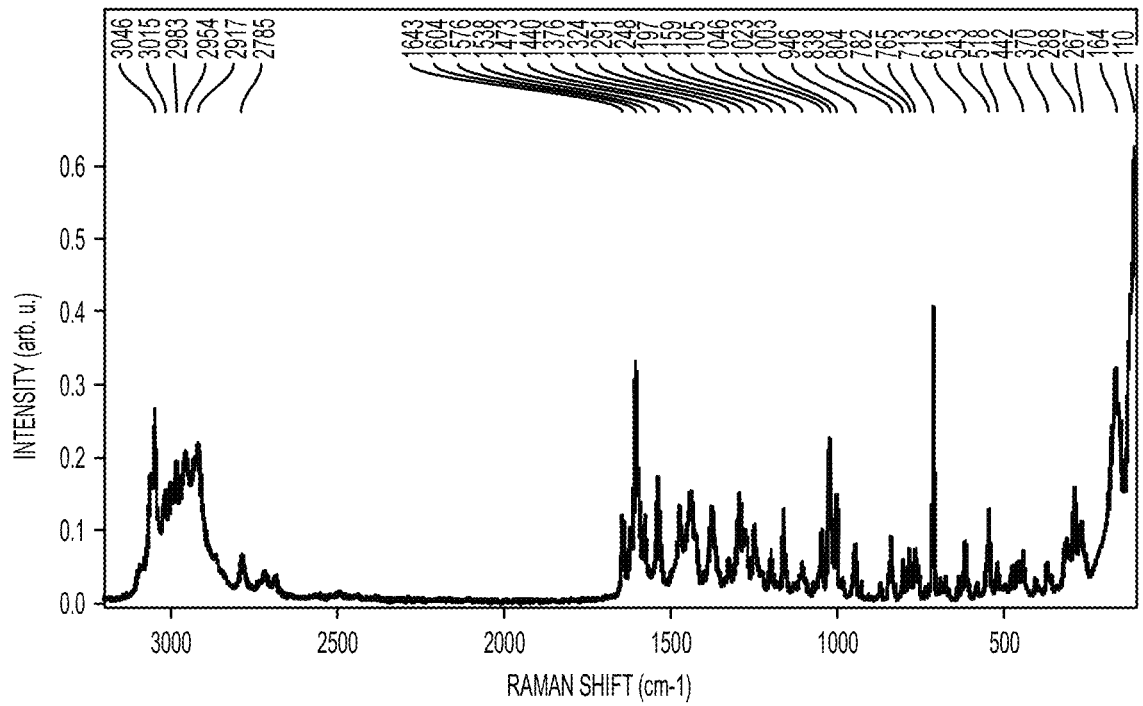
FIG. 21 shows an FT-Raman spectrum for Form III.

In some embodiments, crystalline Form III has an FT-Raman trace substantially as shown in FIG. 21.

Figure 22:
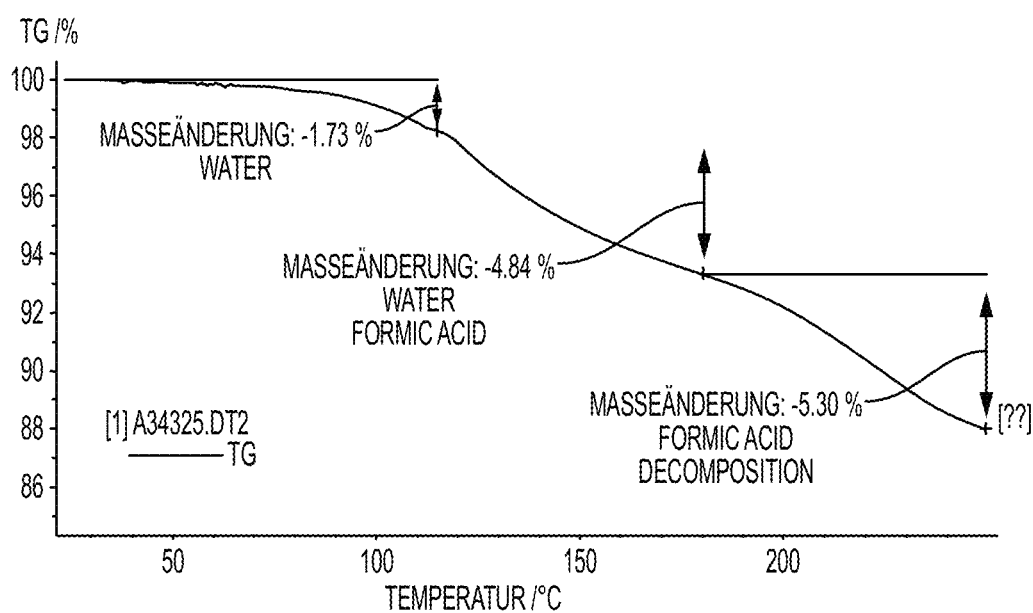
FIG. 22 shows the results of a TGA experiment for Form III.

In some embodiments, crystalline Form III has a TGA trace substantially as shown in FIG. 22.

Methods

The crystalline forms of the invention are NK-1 receptor antagonists particularly useful for treating depression and pain, particularly depression and pain resulting from inflammatory conditions (such as migraine, rheumatoid arthritis, asthma, and inflammatory bowel disease) or disorders of the central nervous system (CNS) (such as Parkinson's disease or Alzheimer's disease). The crystalline forms of Formula I are further useful for the treatment of motion sickness and emesis.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187-214), anxiety (Can. J. Phys., 1997, 75, 612-621) and depression (Science, 1998, 281, 1640-1645). Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases is well established ("Tachykinin Receptor and Tachykinin Receptor Antagonists", J. Auton. Pharmacol., 13, 23-93, 1993). NK-1 receptor antagonists, in particular, are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

NK-1 receptor antagonists are further useful for the treatment of motion sickness and for treatment induced vomiting. The New England Journal of Medicine, Vol. 340, No. 3 190-195, 1999 has been described the reduction of cisplatin-induced emesis by a selective neurokinin-1-receptor antagonist. U.S. Pat. No. 5,972,938 describes a method for treating a psychoimmunologic or a psychosomatic disorder by administration of a tachykinin receptor, such as NK-1 receptor antagonist. Furthermore, the crystalline forms of this invention are useful as agents against headache, anxiety, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases.

Some indications in accordance with the present invention are those which include disorders of the central nervous system, for example indications for the treatment or prevention of certain depressive disorders, anxiety or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

Further examples of NK-1-associated diseases include induced vomiting and nausea, including chemotherapy-induced nausea and vomiting (CINV) which is a common side effect of many cancer treatments. Further examples of NK-1-associated diseases include overactive bladder disorder (OAB or urinary incontinence), which, in some cases, results from sudden, involuntary contraction of the muscle in the wall of the urinary bladder.

Pharmaceutical Formulations and Dosage Forms

When employed as pharmaceuticals, the crystalline forms of the invention can be administered in the form of pharmaceutical compositions. These compositions can be prepared in a manner well known in the pharmaceutical art, and can be administered by a variety of routes depending upon whether local or systemic treatment is desired and upon the area to be treated. Administration can be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the crystalline form of the invention in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active crystalline form, soft and hard gelatin capsules, suppositories, sterile injectable solutions, and sterile packaged powders.

In preparing a formulation, the active crystalline form can be milled to provide the appropriate particle size prior to combining with the other ingredients. If the active crystalline form is substantially insoluble, it can be milled to a particle size of less than 200 mesh. If the active crystalline form is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the crystalline forms or compositions of the invention contain from about 5 to about 500 mg of the active ingredient. One having ordinary skill in the art will appreciate that this embodies crystalline forms or compositions containing from about 50 to about 100, from about 100 to about 150, from about 150 to about 200, from about 200 to about 250, from about 250 to about 300, from about 300 to about 350, from about 350 to about 400, from about 400 to about 450, or from about 450 to about 500 mg of the active ingredient.

In some embodiments, the crystalline forms or compositions of the invention contain from about 500 to about 1000 mg of the active ingredient. One having ordinary skill in the art will appreciate that this embodies crystalline forms or compositions containing from about 500 to about 550, from about 550 to about 600, from about 600 to about 650, from about 650 to about 700, from about 700 to about 750, from about 750 to about 800, from about 800 to about 850, from about 850 to about 900, from about 900 to about 950, or from about 950 to about 1000 mg of the active ingredient.

The active crystalline form can be effective over a wide dosage range and is generally administered in a pharmaceutically effective amount. It will be understood, however, that the amount of the crystalline form actually administered will usually be determined by a physician, according to the relevant circumstances, including the condition to be treated, the chosen route of administration, the actual crystalline form administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a crystalline form of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the crystalline forms and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of crystalline form or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the crystalline form preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the crystalline form of the present invention can vary according to, for example, the particular use for which the treatment is made, the manner of administration of the crystalline form, the health and condition of the patient, and the judgment of the prescribing physician. The proportion or concentration of a crystalline form of the invention in a pharmaceutical composition can vary depending upon a number of factors including dosage, chemical characteristics (e.g., hydrophobicity), and the route of administration. For example, the crystalline forms of the invention can be provided in an aqueous physiological buffer solution containing about 0.1 to about 10% w/v of the crystalline form for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the crystalline form selected, formulation of the excipient, and its route of administration. Effective doses can be extrapolated from dose-response curves derived from in vitro or animal model test systems.

The crystalline forms of the invention can also be formulated in combination with one or more additional active ingredients which can include any pharmaceutical agent such as antibodies, immune suppressants, anti-inflammatory agents, drugs used for the treatment of rheumatoid arthritis, disorders of the central nervous system and the like.

Labeled Compound and Assay Methods

Another aspect of the present invention relates to labeled crystalline forms of the invention (radio-labeled, fluorescent-labeled, etc.) that would be useful not only in imaging techniques but also in assays, both in vitro and in vivo, for localizing and quantifying NK-1 in tissue samples, including human, and for identifying NK-1 ligands by inhibition binding of a binding of a labeled compound. Accordingly, the present invention includes NK-1 receptor assays that contain such labeled compounds.

The present invention further includes isotopically-labeled crystalline forms of Formula I. An "isotopically" or "radio-labeled" crystalline form is a crystalline form of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{8}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled crystalline form will depend on the specific application of that radio-labeled crystalline form. For example, for in vitro NK-1 receptor labeling and competition assays, crystalline forms that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled crystalline form" is a crystalline form that has incorporated at least one radionuclide. In some embodiments the radionuclide is selected from the group consisting of $^{3}H$, $^{14}C$, $^{125}I$, $^{35}S$ and $^{82}Br$. Synthetic methods for incorporating radioisotopes into organic compounds are applicable to crystalline forms of the invention and are well known in the art.

A radio-labeled crystalline form of the invention can be used in a screening assay to identify/evaluate compounds. In general terms, a newly synthesized or identified compound (i.e., test compound) can be evaluated for its ability to reduce binding of the radio-labeled compound of the invention to the NK-1 receptor. Accordingly, the ability of a test compound to compete with the radio-labeled compound for binding to the NK-1 receptor directly correlates to its binding affinity.

Kits

The present invention also includes pharmaceutical kits useful, for example, in the treatment or prevention of NK-1-associated diseases which include one or more containers containing a pharmaceutical composition comprising a therapeutically effective amount of a crystalline form of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

In the below examples, analytical grade solvents purchased from Fluka, ABCR or Merck were used unless otherwise stated.

X-Ray Powder Diffraction (XRPD) patterns were recorded in transmission geometry on a STOE STADI P diffractometer with CuKα radiation (1.54 Å) and a position sensitive detector. The samples (approximately 50 mg) were prepared between thin polymer films and analyzed without further processing (e.g., grinding or sieving) of the substance unless otherwise indicated.

XRPD patterns were alternatively recorded on a Bruker D8 diffractometer with CuKα radiation (40 kV/40 mA) and a LynxEye detector. Alternatively, XRPD patterns were recorded on a X'Pert PRO diffractometer using a PW3065 Goniometer.

Differential Scanning Calorimetry (DSC) was carried out on a Mettler-Toledo differential scanning calorimeter DSC820 with a FRS05 sensor. System suitability tests and calibrators were carried out according to the internal standard operation procedure. The general experimental conditions were 30° C. to a maximum temperature of either 180 or 220° C. at 5 K/min or 10K/min nitrogen gas flow at 100 mL/min, using an aluminum sample pan.

Thermogravimetric analysis (TGA) was carried out on a Mettler-Toledo thermogravimetric analyzer (TGA850/SDTA) with the following conditions: Ramp at 5 K/min to 220° C.; nitrogen gas at 50 mL/min sample purge flow; aluminum sample pan.

TGA measurements were alternatively conducted on a Netzsch Thermo-Microbalance TG 209 coupled to a Bruker FTIR Spectrometer Vector 22 using the following conditions: Ramp at 10° C./min under nitrogen; aluminum sample pan equipped with pinholes.

Infrared (IR) spectra were recorded as film of a suspension in Nujol consisting of approximately 15 mg of sample and approximately 15 mg of Nujol between two sodium chloride plates, with a FTIR spectrometer Nicolet 20SXB in transmittance (resolution 2 cm$^{-1}$, 200 or more co-added scans, MTC detector). Alternatively, the spectra were recorded without preparation in attenuated total reflection mode (ATR) with an FTIR spectrometer equipped with an IR-Microscope (Nic-Plan Nicolet) (resolution 2 cm$^{-1}$, 200 or more co-added scans, MTC detector).

Single crystal structure analysis was collected on a STOE Image Plate Diffraction System (STOE, Darmstadt) with Mo-radiation (0.71 Å) and data processed with STOE IPDS-software. The crystal structure was solved and refined with ShelXTL (Bruker AXS, Karlsruhe).

Moisture Adsorption/Desorption data was collected on a DVS-1 (SMS Surface Measurements Systems) moisture balance system. The sorption/desorption isotherms were measured stepwise in a range of 0% RH to 90% RH at 25° C. A weight change of <0.002 mg/min was chosen as the criterion to switch to the next level of relative humidity (with a maximum equilibration time of 6 hours if the weight criterion was not met). The data were corrected for the initial moisture content of the samples so that the weight after drying the sample at 0% relative humidity was taken as the zero point. The hygroscopicity of a given substance was characterized, in accordance with the European Phamacopoeia (Technical Guide 1999), by the increase in mass when the relative humidity is raised from 0% RH to 90% RH, as defined below (where weight increase=x):

Non hygroscopic: $x<0.2\%$

Slightly hygroscopic: $0.2\% \leq x < 2.0\%$

Hygroscopic: $2.0\% \leq x < 15\%$

Very hygroscopic: $x \geq 15.0\%$

Deliquescent: Sufficient liquid as adsorbed to form a liquid

FT-Raman Spectra were recorded on a Bruker RFS 100 FT-Raman system with a near infrared Nd:YAG laser operating at 1064 nm and a liquid nitrogen-cooled germanium detector. For each sample, 64 scans with a resolution of 2 cm$^{-1}$ were accumulated. 300 mW laser power was used. The FT-Raman data are shown in the region between 3500 to 100 cm$^{-1}$.

NMR spectra were recorded using a Bruker DPX300 spectrometer.

Example 1

Preparation and Characterization of Form I

Crystalline Form I was prepared by combining 179 g of the compound of Formula I with toluene (179 g) and n-heptane (585 g) and the solution was heated to reflux temperature and filtered to afford a clear solution. The solution was then cooled to −10° C. at 10 K/h. After aging of the suspension for 1 h at this temperature, crystals were isolated and dried at 80° C./10 mbar overnight.

Form I was confirmed as a crystalline solid according to XRPD analysis. The XRPD pattern of Form I is shown in FIG. 1 and the peak data is given below in Table 1.

TABLE 1

XRPD Peak Data for Form I.

| Peak No. | 2-Theta |
|---|---|
| 1 | 4.5 |
| 2 | 8.4 |
| 3 | 11.5 |
| 4 | 13.1 |
| 5 | 13.9 |
| 6 | 14.8 |
| 7 | 16.7 |
| 8 | 17.4 |
| 9 | 17.7 |
| 10 | 19.5 |
| 11 | 21.2 |
| 12 | 21.6 |
| 13 | 21.8 |

DSC analysis of Form I revealed one melting endotherm peak with an onset temperature of 159.5° C. (varying between 158.3-160.6° C.) and a maximum at 160.3° C. (varying between 159.9-162.6). The DSC thermogram is provided in FIG. 2.

TGA analysis of Form I revealed a <0.1% weight loss up to 140° C. After melting, a continuous weight loss above 160° C. indicated the starting decomposition of the compound. The TGA thermogram is provided in FIG. 3.

Moisture adsorption/desorption of Form I was analyzed by DVS. Results from two DVS cycles are shown in FIG. 4. The data indicates that, during the drying step and the first adsorption segment, Form I exhibits a weight gain of about 0.3% which is likely due to electrostatic charges. A 0.1% weight loss was observed in the second cycle. The shapes of the isotherms indicated that Form I is non-hygroscopic and unsolvated.

Figure 5:
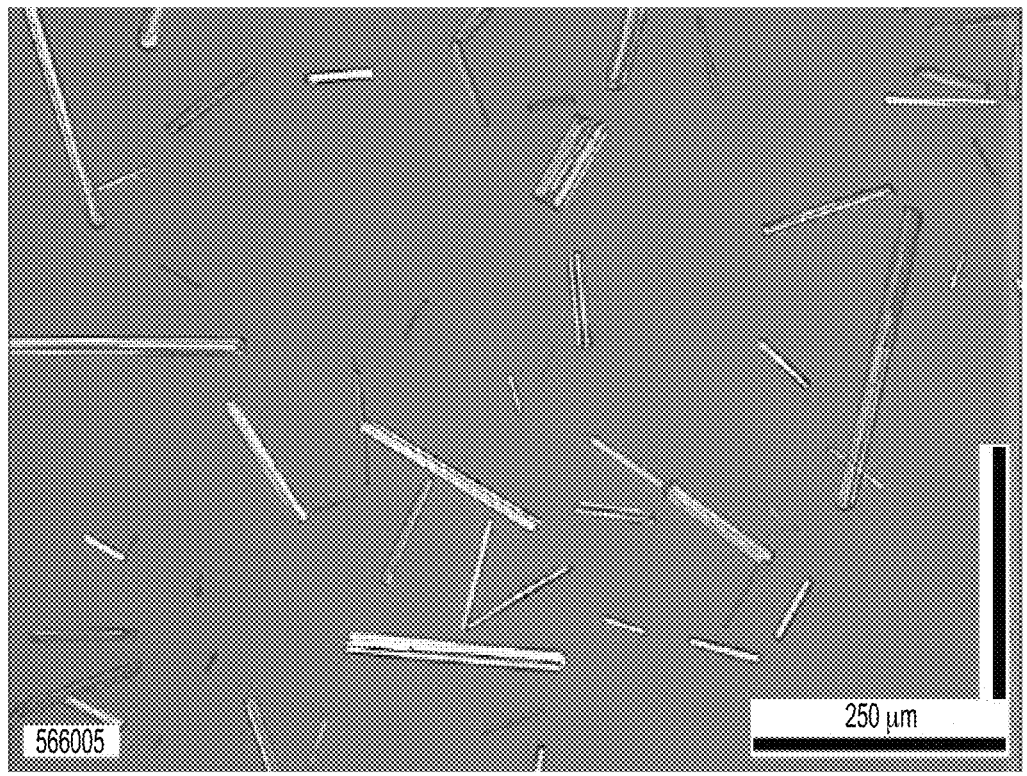
FIG. 5 shows a microphotograph of Form I.
Figure 6A:
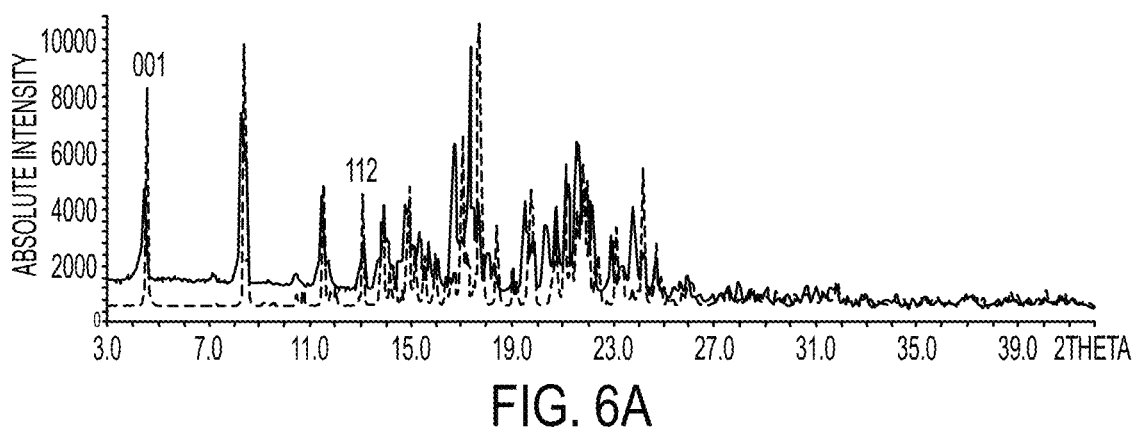
FIG. 6 shows (A) an overlay of a measured XRPD pattern for Form I (red) and the theoretical pattern (blue, calculated based on the single crystal structure at cryogenic temperature); and (B) theoretical powder diffraction peaks and their Miller indices (hkl) as calculated from the crystal structure.
Figure 6B:
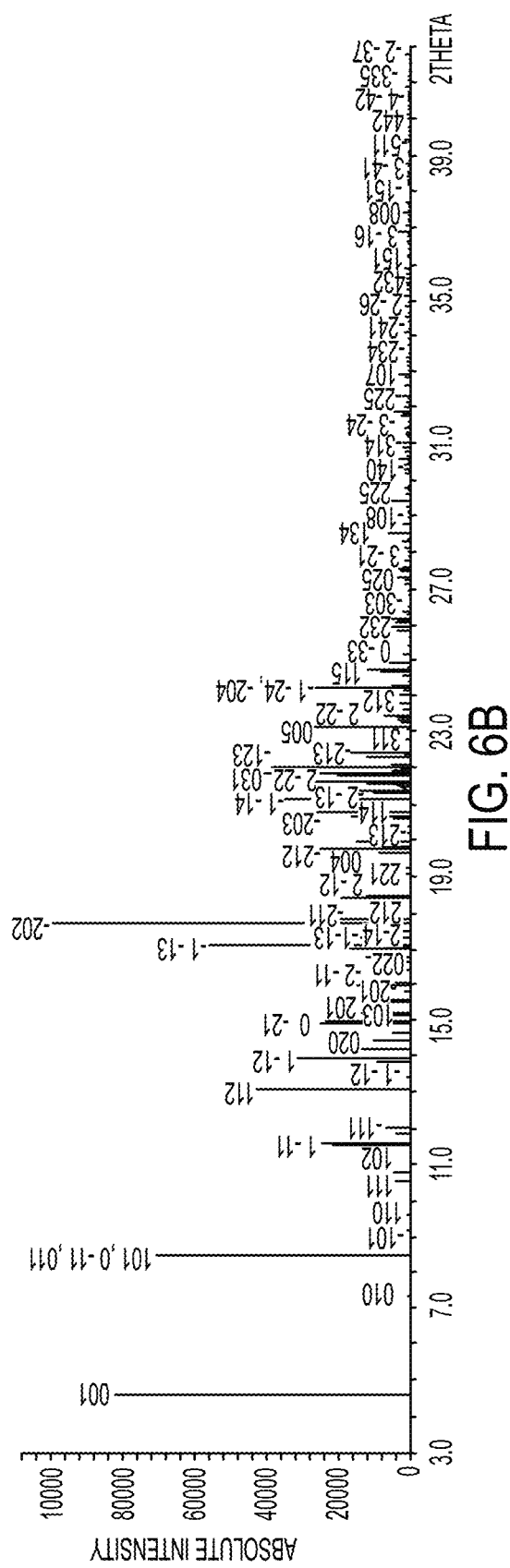

Single crystal parameters for Form I are shown in Table 2. A microphotograph showing Form I crystals is provided in FIG. 5. The theoretical powder pattern calculated based on the crystal structure matches the measured powder pattern well and allows the assignment of Miller indices (hkl) to some reflections (FIG. 6). Small differences in peak positions between theoretical and measured patterns are believed to be due to the changes in dimension of the crystal unit cell when changing the temperature from room temperature to 150 K and make the assignment of indices of reflections at higher 2θ values difficult. An overlay of the measured XRPD pattern of Form I and the theoretical pattern of Form I based on the single crystal structure at cryogenic temperature is shown in FIG. 6.

TABLE 2

Single Crystal Parameters of Form I.

| Parameter | Measurement |
|---|---|
| Crystal system | Triclinic |
| Space group | P-1 |
| Crystal habit | Needle Like |
| Unit cell dimensions (Å) | a = 12.173 |
|  | b = 12.556 |
|  | c = 19.247 |
| (°) | α = 89.97 |
|  | β = 87.38 |
|  | γ = 83.34 |
| Temperature (K) | 150 |
| Cell volume (Å$^3$) | 2918 |

TABLE 2-continued

Single Crystal Parameters of Form I.

| Parameter | Measurement |
|---|---|
| Molecules in cell unit | 4 |
| Density (calculated) (g/cm$^3$) | 1.317 |

Figure 7:
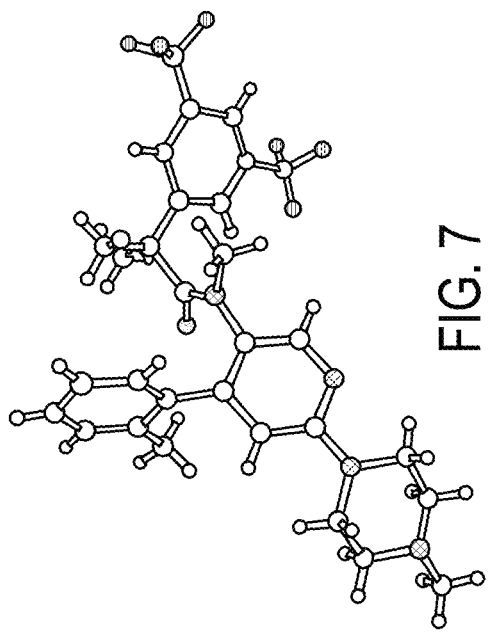
FIG. 7 shows a ball and stick representation of the crystal structure of Form I.
Figure 8:
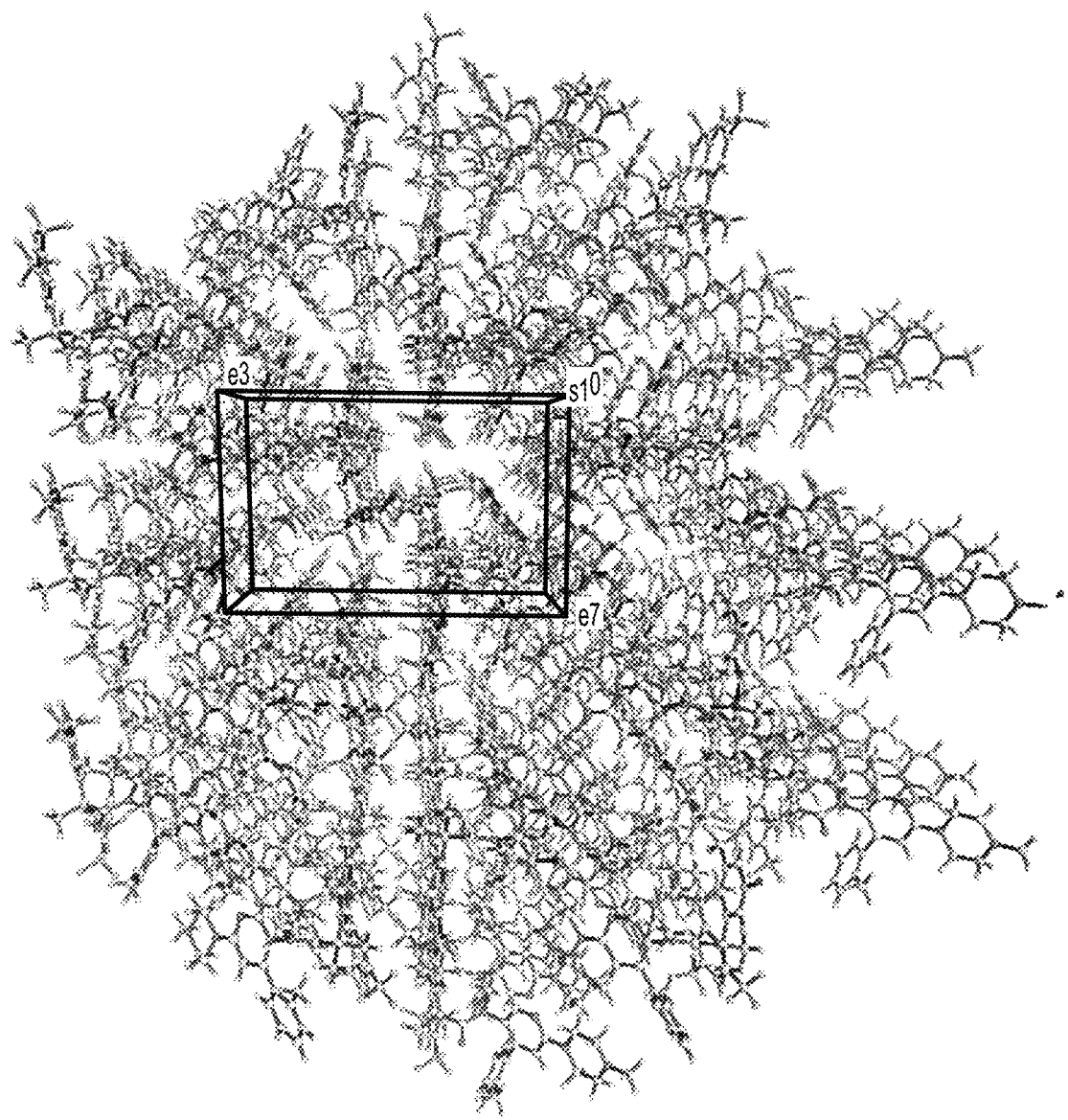
FIG. 8 shows crystal packing in the crystal of Form I. The crystallographic cell unit is shown in red.

Crystals of Form I were found to contain two molecules per asymmetric unit. No solvent molecules are present in the crystal lattice. The two molecules per asymmetric unit both assume a similar conformation as shown in FIG. 7. The crystal packing contacts are mainly hydrophobic and several interactions between fluorine atoms in the crystal lattice packing are visible as shown in FIG. 8.

IR analysis of Form 1 revealed specific bands at about 1647, 1610, 1598, 1534, 1500, 1403, 1375, 1367, 1339, 1330, 1278, 1233, 1187, 1171, 1149, 1081, 1005, 902, 895, 845, 803, 769, 711, and about 706 cm$^{-1}$. The IR spectrum is shown in FIG. 9.

The NMR spectrum of Form I is shown in FIG. 10.

Selected physicochemical data of Form I is summarized below in Table 3.

TABLE 3

Physicochemical data of Form I.

| Parameter | Measurement |
|---|---|
| Melting temperature by DSC (° C.) | T$_{onset}$ = 159.5 (158.3-160.6) T$_{extrapol.\ peak}$ = 160.3 (159.9-162.6) |
| Heat of fusion (kJ/mol) | 36.7 (34.8-37.4) |
| Entropy of fusion J/(mol*K) | 84.6 |
| Weight loss between 25° C. and 140° C. (%) | <0.1 (<0.1-0.2) |
| Density (g/cm$^3$) | Calculated = 1.317 Measured = 1.33 |
| Hygroscopicity (weight change 0 to 90%-RH classification) (%) | 0.1 (non-hygroscopic) |
| FTIR spectrum (cm$^{-1}$) | 1647, 1610, 1598, 1534, 1500, 1403, 1375, 1367, 1339, 1330, 1278, 1233, 1187, 1171, 1149, 1081, 1005, 902, 895, 845, 803, 769, 711, and about 706 |
| XRPD peaks (2θ) | 4.5, 8.4, 11.5, 13.1, 13.9, 14.8, 16.7, 17.4, 17.7, 19.5, 21.2, 21.6, 21.8 |

Samples of Form I were equilibrated in various solvents at 25° C. or 60° C. to test the solubility of Form I in the solvents. Solubility was determined gravimetrically. A weighted sample of Form I was suspended in a defined amount of solvent. After equilibration and solvent-liquid separation, the weight of the saturated liquid was determined. The solvent was then evaporated, the solid residue dried to dryness and weighed. Results of the solubility experiments are shown in Tables 4 and 5. The solubility is reported as weight of solid substance dissolved divided by the weight of the solution.

TABLE 4

Solubility of Form I at 25° C.

| Solvent | Solubility (% m/m) |
|---|---|
| Water | <0.1 |
| Ethanol | >11.5 |
| Methanol | >11.9 |
| 2-Propanol | N/A |
| 1-Butanol | >11.6 |
| Acetone | >11.1 |
| N,N-Dimethylformamide | >9.9 |
| Trifluoroethanol | >7.5 |
| Tetrahydrofuran | >9.9 |
| Acetonitrile | 9 |
| Dioxane | >9.0 |
| Dichloroethane | >7.0 |
| Ethyl Acetate | N/A |
| 2-Butanone | >11.2 |
| Toluene | >10.8 |
| Water/Acetonitrile 2:1 | 0.5 |
| Water/Acetonitrile 1:2 | 6.2 |
| Water/Dioxane 2:1 | 0.1 |
| Water/Dioxane 1:2 | 4.9 |
| Water/Ethanol 2:1 | 0.1 |
| Water/Ethanol 1:2 | 3.1 |
| Water/Methanol 2:1 | 0.2 |
| Water/Methanol 1:2 | 1.0 |
| Water/Acetone 2:1 | 0.2 |
| Water/Acetone 1:2 | 7.0 |
| Heptane | 1.2 |
| Cyclohexane | 4.2 |
| Isopropyl Acetate | 22.2 |
| Xylene | 18.4 |

TABLE 5

Solubility of Form I at 60° C.

| Solvent | Solubility (% m/m) |
|---|---|
| Water | <0.1 |
| Ethanol | 33.1 |
| Methanol | 48.4 |
| 2-Propanol | 26.2 |
| 1-Butanol | 29.9 |
| Acetone | >53.3 |
| N,N-Dimethylformamide | 40.7 |
| Trifluoroethanol | >39.1 |
| Tetrahydrofuran | >50.4 |
| Acetonitrile | 14.4 |
| Dioxane | >41.6 |
| Dichloroethane | 34.7 |
| Ethyl Acetate | 45.9 |
| 2-Butanone | >52.6 |
| Toluene | 48.8 |
| Water/Acetonitrile 2:1 | <0.1 |
| Water/Acetonitrile 1:2 | 6.4 |
| Water/Dioxane 2:1 | <0.1 |
| Water/Dioxane 1:2 | 21.1 |
| Water/Ethanol 2:1 | <0.1 |
| Water/Ethanol 1:2 | 5.5 |
| Water/Methanol 2:1 | <0.1 |
| Water/Methanol 1:2 | 0.4 |
| Water/Acetone 2:1 | <0.1 |
| Water/Acetone 1:2 | 11.7 |
| Heptane | 3.0 |
| Cyclohexane | 16.0 |
| Isopropyl Acetate | >35.0 |
| Xylene | >35.0 |

Example 2

Preparation and Characterization of Amorphous Form

The amorphous form of the compound of Formula I was prepared by dissolving Form I (5 g) in dioxane (50 mL) in an ultrasonic bath. After filtration, the resulting clear solution was frozen (dry ice/acetone bath) and dried.

The amorphous nature of the material was confirmed by XRPD analysis. The XRPD pattern of the amorphous form of the compound of Formula I shown in FIG. 11.

DSC analysis of the amorphous form of the compound of Formula I revealed a one melting endotherm peak with an onset temperature of 41.4° C. and a maximum at 46.4° C. In particular, upon heating the amorphous form of the compound of Formula I to 70° C., a glass transition was observed between about 50° C. and 65° C. The sample was cooled to 0° C. and then reheated to yield a glass transition between about 40° C. and 60° C. with minimal relation enthalpy allowing a more accurate determination of the glass transition temperature (midpoint 46.4). Upon further heating, the sample crystallized in the temperature range of about 80° C. to about 120° C. to yield Form I. The DSC thermogram of the amorphous form is provided in FIG. 12.

Figure 13:
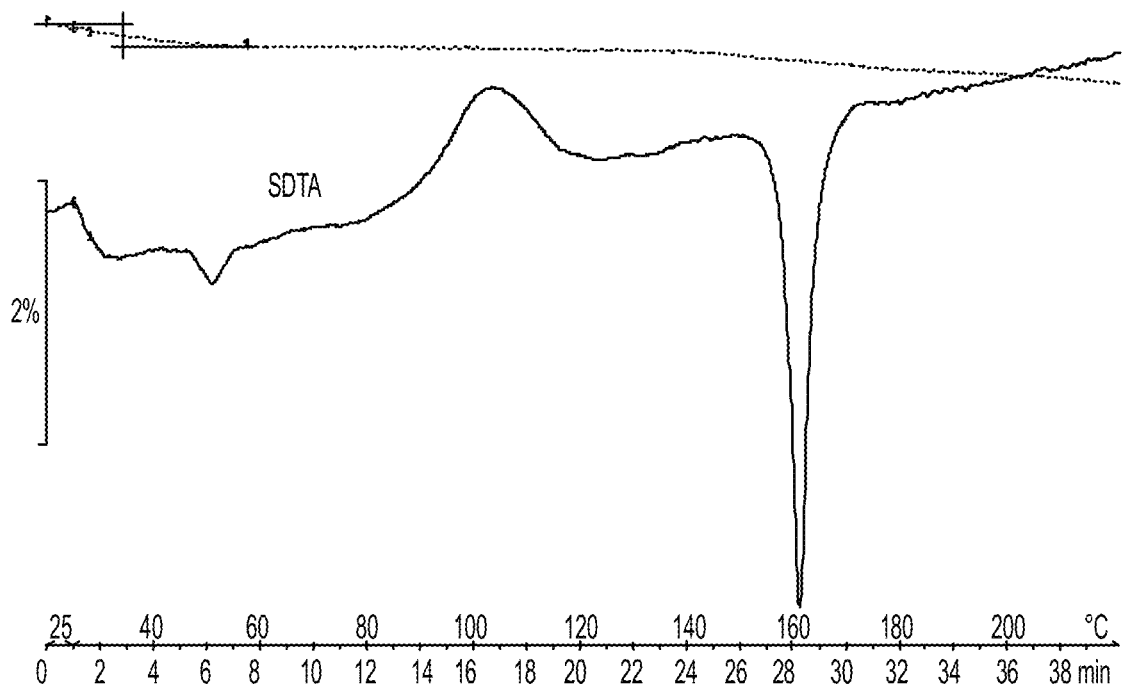
FIG. 13 shows the results of a TGA experiment for amorphous Formula I.

The TGA thermogram of the amorphous form of the compound of Formula I is provided in FIG. 13.

Figure 14:
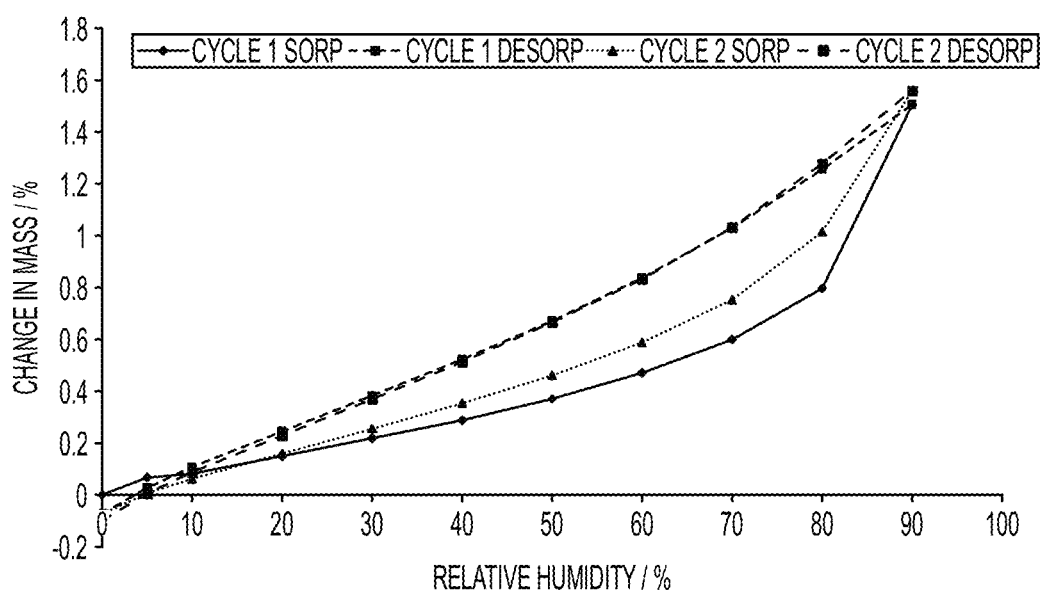
FIG. 14 shows the results of a DVS experiment for amorphous Formula I.

Moisture adsorption/desorption of Form I was analyzed by DVS. Results from two DVS cycles are shown in FIG. 14. The data indicates that, the amorphous material adsorbs up to 1.5% w/w of moisture. No crystallization could be observed during the sorption isotherm measurement.

Figure 15:
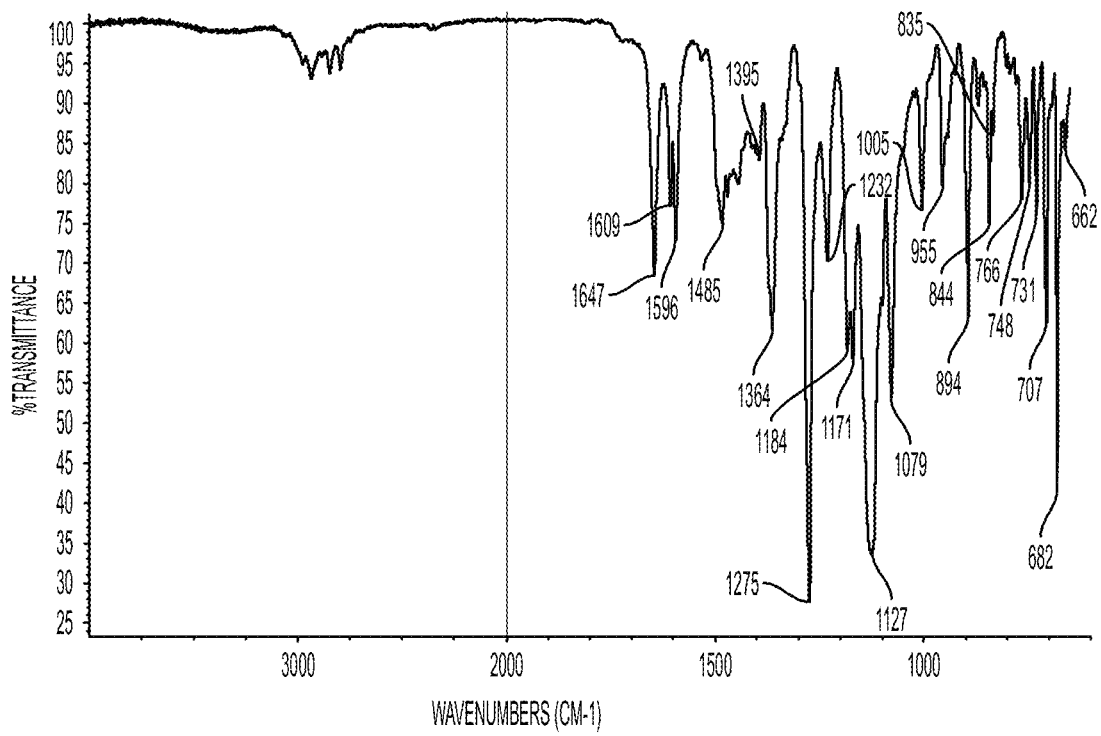
FIG. 15 shows an IR spectrum for amorphous Formula I.

The IR spectrum of the amorphous form of the compound of Formula I revealed specific bands at about 1647, 1609, 1596, 1484, 1395, 1364, 1275, 1232, 1184, 1171, 1127, 1079, 1005, 956, 894, 844, 766, 748, 731, and about 708 cm$^{-1}$. The IR spectrum is shown in FIG. 15.

Figure 16:
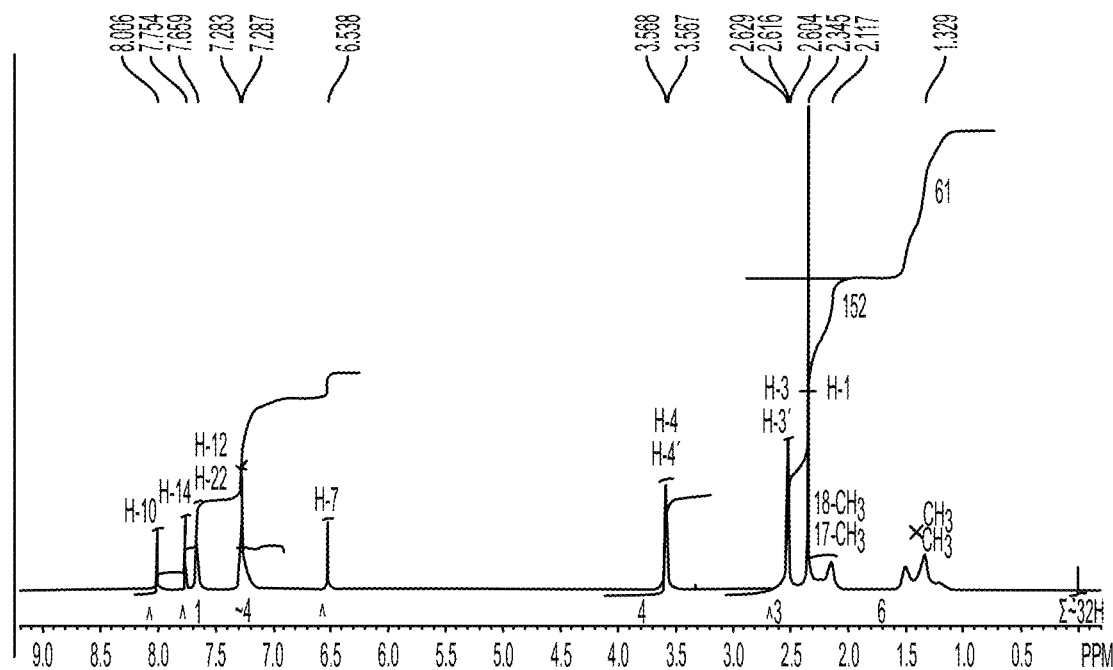
FIG. 16 shows an NMR spectrum for amorphous Formula I.

The NMR spectrum of the amorphous form of the compound of Formula I is shown in FIG. 16.

Selected physicochemical data of the amorphous form of the compound of Formula I is summarized below in Table 6.

TABLE 6

Physicochemical Data of Amorphous Form.

| Parameter | Measurement |
|---|---|
| Weight loss between 25° C. and 140° C. (%) | 0.2 |
| Glass transition temperature (° C.) | 46.4 |
| Hygroscopicity (weight change 0 to 90%-RH classification) (%) | 1.5 (slightly hygroscopic) |
| FTIR spectrum (cm$^{-1}$) | 1647, 1609, 1596, 1484, 1395, 1364, 1275, 1232, 1184, 1171, 1127, 1079, 1005, 956, 894, 844, 766, 748, 731, 708 |

Example 3

Preparation and Characterization of Form II

Crystalline Form II was prepared by dissolving trifluoroethanol in water at a 5:4 ratio at 70° C., and cooling at 3° C./hour. An emulation was initially obtained, partial evaporation and additional of trifluoroethanol/water at room temperature led to Form II. Form II was found to be a crystalline trifluoroethanol solvate.

Form II was confirmed as a crystalline solid according to XRPD analysis. The XRPD pattern of Form II is shown in FIG. 17 and the peak data is given below in Table 7. Form II was found to be unstable under ambient conditions and converts to Form I. FIG. 17 shows the XRPD pattern of Form II (black) in comparison with Form I (blue). The red pattern was recorded after storing Form II for 1 h and 20 min under ambient conditions. A partial conversion to Form I was observed.

TABLE 7

XRPD Peak Data for Form II.

| 2-Theta | H % |
|---|---|
| 4.0 | 39.5 |
| 14.7 | 33.8 |
| 15.5 | 34 |
| 16.6 | 40.1 |
| 17.0 | 48.3 |
| 17.4 | 33.2 |
| 18.2 | 81.4 |
| 19.9 | 80.3 |
| 20.4 | 60.6 |
| 20.8 | 38.2 |
| 21.2 | 100 |
| 21.7 | 69.6 |
| 23.9 | 62.8 |

FT-Raman Spectroscopy analysis of Form II is provided in FIG. 18 with the most pronounced Raman peaks labeled in the figure. The FT-Raman data are shown in the region between 3500 and 100 cm$^{-1}$.

TGA analysis of Form II revealed a 41% weight loss up to 130° C. The weight loss is attributed to water and trifluoroethanol (monohydrate: 3%, monosolvate: 14.7%). The TGA thermogram of Form II is provided in FIG. 19.

Form II was found to convert to Form I at 80% relative humidity. Thermogravimetry coupled to Fourier Transform (TGA-FT) measurements taken during the conversion show a loss of trifluoroethanol above 100° C. Form II was also found to convert to Form I upon suspension equilibration in water.

Example 4

Preparation and Characterization of Form III

Crystalline Form III was prepared by cooling a solution of Form I in a formic acid/water mixture to 4° C.

Form III was found to be a formate salt.

Form III was confirmed as a crystalline solid according to XRPD analysis. The XRPD pattern of Form III is shown in FIG. 20 and the peak data is given below in Table 8.

The approximate solubility of Form III in water at rt is below 1 mg/mL.

TABLE 8

XRPD Peak Data for Form III.

| 2-Theta | H % |
|---|---|
| 4.0 | 58.6 |
| 8.0 | 70.9 |
| 10.0 | 32.7 |
| 12.0 | 67.9 |
| 15.3 | 71 |
| 16.0 | 100 |
| 16.7 | 37.7 |
| 18.4 | 57.8 |
| 21.9 | 43.5 |

TABLE 8-continued

XRPD Peak Data for Form III.

| 2-Theta | H % |
|---|---|
| 22.1 | 65 |
| 23.3 | 54.2 |
| 23.4 | 72.4 |
| 23.6 | 31.5 |
| 24.2 | 35.4 |

FT-Raman Spectroscopy analysis of Form III is provided in FIG. 21 with the most pronounced Raman peaks labeled in the figure. The FT-Raman data are shown in the region between 3500 and 100 cm$^{-1}$.

$^1$H and $^{13}$C-NMR spectroscopy of Form III were found to be consistent with the formation of a monosalt.

TGA analysis of Form III revealed a 1.7% weight loss up to 115° C. The weight loss is consistent for a non-stoichiometric hydrate or for surface adsorbed water. Above 115° C. a mass loss of about 10% is observed, which is attributable to formic acid, water and decomposition (theoretical mass loss for a monosalt: 7.4% formic acid). The TGA thermogram of Form III is provided in FIG. 22

Example 5

Supplemental Characterization of Form I

A micronized sample of Form I was characterized by Powder X-Ray Diffraction (XRPD). The XRPD spectrum for Form I is provided in FIG. 23 and the corresponding peak data is provided below in Table 9.

TABLE 9

XRPD Peak Data for Form I.

| 2-Theta | H % |
|---|---|
| 4.5 | 35.3 |
| 8.4 | 57.6 |
| 11.4 | 41.5 |
| 13.1 | 35.3 |
| 13.9 | 37.6 |
| 14.7 | 36.2 |
| 16.7 | 72.9 |
| 17.3 | 100 |
| 17.6 | 42.7 |
| 19.5 | 45.8 |
| 20.7 | 55.6 |
| 21.2 | 55 |
| 21.5 | 86 |
| 21.8 | 62 |
| 22.1 | 39.5 |
| 22.9 | 45.7 |
| 23.7 | 55.3 |

FT-Raman Spectroscopy analysis of Form I is provided in FIG. 24 with the most pronounced Raman peaks labeled in the figure. The FT-Raman data are shown in the region between 3500 and 100 cm$^{-1}$.

The pKa of Form I was calculated to be 6.1 and 7.9. PKa calculations were conducted using an ACD/Labs device (Release 10; Product Version 10).

Example 6

Supplemental Characterization of Form I

The compound of Formula I (Form I) was further characterized by the procedures described below. A micronized batch of the compound of Formula I (batch #27005937 from Helsinn Chemicals SA) was used as the starting material in the characterization experiments unless otherwise noted.

Figure 28:
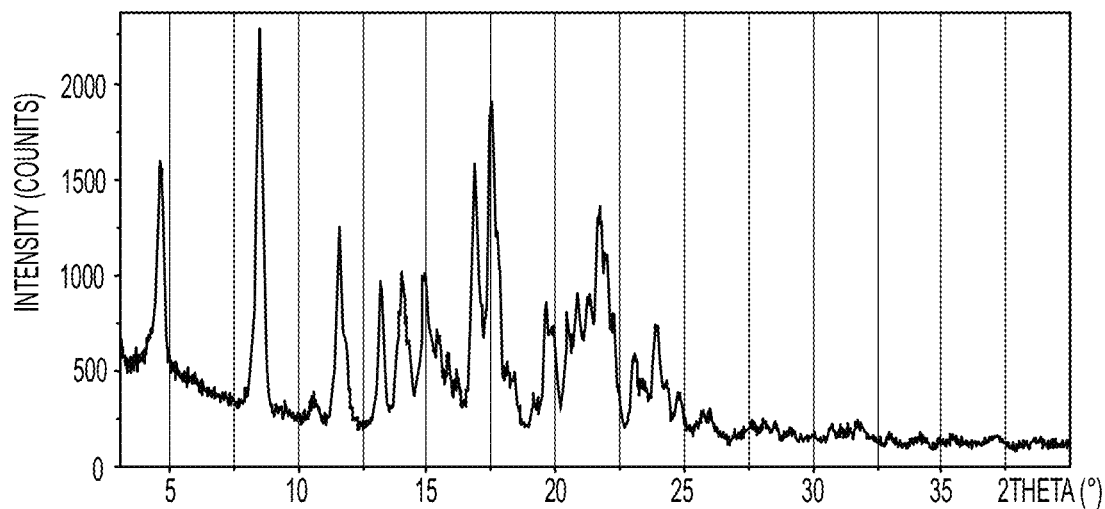
FIG. 28 shows an XRPD pattern for a micronized sample of Form I.

The micronized sample (Form I) was characterized by XRPD. The XRPD spectrum is provided in FIG. 28 and the associated peaks are shown below in Table 10.

TABLE 10

XRPD Peak Data for Micronized Sample.

| 2-Theta | Height (cts) | H % |
|---|---|---|
| 4.6 | 1047.62 | 53.59 |
| 8.5 | 1954.88 | 100.00 |
| 10.6 | 90.86 | 4.65 |
| 11.6 | 1016.25 | 51.99 |
| 13.2 | 658.90 | 33.71 |
| 14.0 | 686.68 | 35.13 |
| 14.8 | 553.25 | 28.30 |
| 15.5 | 340.72 | 17.43 |
| 15.8 | 263.63 | 13.49 |
| 16.2 | 127.06 | 6.5 |
| 16.8 | 1191.76 | 60.96 |
| 17.5 | 1460.76 | 74.72 |
| 17.8 | 773.60 | 39.57 |
| 18.4 | 245.75 | 12.57 |
| 19.1 | 137.2 | 7.02 |
| 19.6 | 580.31 | 29.69 |
| 19.9 | 474.34 | 24.26 |
| 20.5 | 466.73 | 23.87 |
| 20.8 | 617.14 | 31.57 |
| 21.3 | 626.52 | 32.05 |
| 21.7 | 1059.15 | 54.18 |
| 22.0 | 845.02 | 43.23 |
| 22.3 | 493.18 | 25.23 |
| 23.0 | 335.23 | 17.15 |
| 23.9 | 481.59 | 24.64 |
| 24.3 | 211.54 | 10.82 |
| 24.8 | 148.87 | 7.62 |
| 25.7 | 97.43 | 4.98 |
| 26.0 | 131.94 | 6.75 |
| 27.7 | 69.51 | 3.56 |
| 28.1 | 75.40 | 3.86 |
| 28.5 | 62.66 | 3.21 |
| 29.2 | 41.70 | 2.13 |
| 30.7 | 51.99 | 2.66 |
| 31.8 | 71.50 | 3.66 |
| 33.0 | 34.37 | 1.76 |
| 34.3 | 46.79 | 2.39 |
| 35.4 | 41.40 | 2.12 |
| 37.2 | 49.38 | 2.53 |
| 38.8 | 29.80 | 1.52 |

FT-IR analysis of Form I used in the experiments below revealed specific bands as shown in Table 11. The FT-IR spectrum of Form I is shown in FIG. 25.

TABLE 11

FT-IR Analysis of Form I.

| Wavenumber (cm$^{-1}$) | Intensity |
|---|---|
| 662.2 | 81.3 |
| 681.6 | 57.3 |
| 695.9 | 82.6 |
| 710.1 | 61.8 |
| 730.9 | 72.2 |
| 745.7 | 72.5 |
| 766.7 | 70.2 |
| 802.8 | 85.3 |
| 834.5 | 80.1 |
| 844.1 | 75.9 |
| 857.0 | 84.8 |
| 870.9 | 85.4 |
| 894.0 | 65.2 |
| 901.1 | 65.1 |

TABLE 11-continued

FT-IR Analysis of Form I.

| Wavenumber (cm$^{-1}$) | Intensity |
|---|---|
| 924.2 | 86.5 |
| 956.9 | 75.8 |
| 1004.8 | 70.8 |
| 1049.6 | 82.1 |
| 1079.6 | 54.1 |
| 1100.1 | 63.8 |
| 1134.6 | 34.2 |
| 1170.5 | 51.3 |
| 1185.4 | 53.8 |
| 1231.7 | 66.2 |
| 1275.9 | 30.8 |
| 1330.3 | 85.6 |
| 1364.7 | 59.9 |
| 1401.5 | 80.0 |
| 1443.6 | 80.0 |
| 1471.9 | 77.7 |
| 1499.2 | 75.6 |
| 1533.2 | 91.7 |
| 1597.2 | 75.5 |
| 1609.5 | 75.4 |
| 1646.2 | 62.7 |
| 2793.9 | 91.2 |
| 2845.8 | 92.1 |
| 2931.9 | 92.4 |
| 2974.3 | 94.7 |

Grounded Form I

Figure 26:
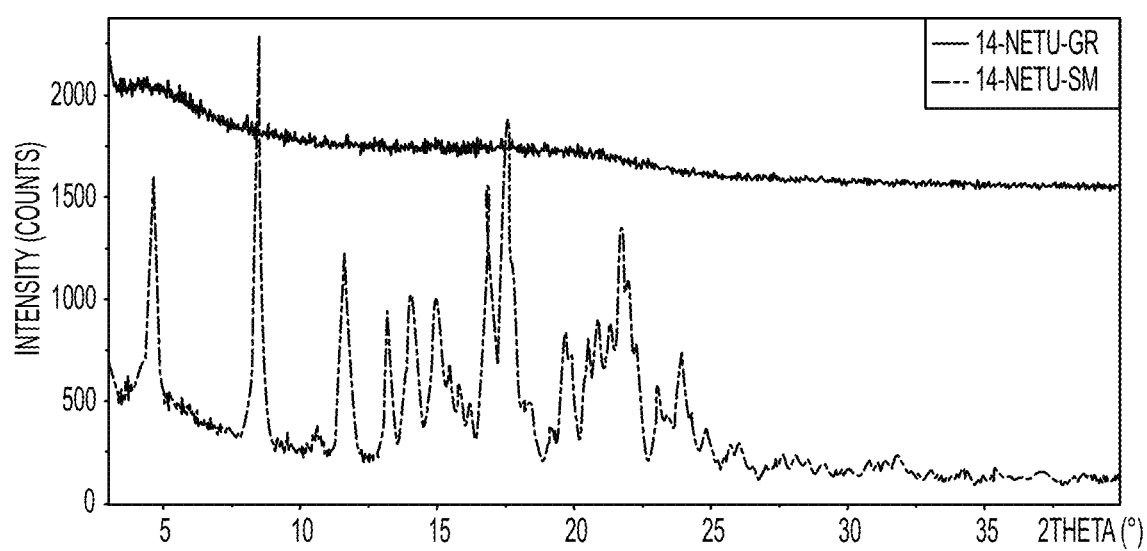
FIG. 26 shows an XRPD comparison between a Form I reference sample (black line) and a ground sample (blue line).

An untreated sample of Form I was ground by ball milling in a Retsch MN 200 grinder for 10 min at a frequency of 30 Hz. The sample was then analyzed by XRPD to determine its diffraction pattern. The stability of the ground sample was determined by comparing the diffraction pattern of the ground sample with that of the reference sample. As shown in FIG. 26, grinding caused loss of crystallinity of the sample. In FIG. 26, the XRPD pattern for the Form I reference sample is shown in black and the pattern for the ground sample is shown in blue.

Kneaded Form I

Figure 27:
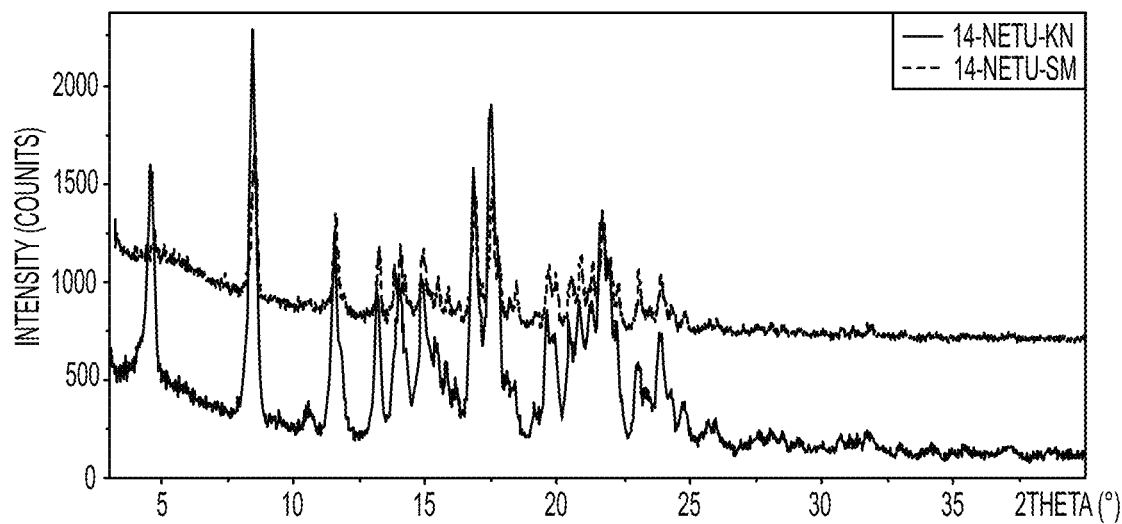
FIG. 27 shows an XRPD comparison between a Form I reference sample (black line) and a kneaded sample (red line).

An untreated sample of Form I was ground by ball milling in a Retsch MN 200 grinder for 10 min at a frequency of 30 Hz with a catalytic amount of water. The sample was then analyzed by XRPD to determine its diffraction pattern. The stability of the kneaded sample was determined by comparing the diffraction pattern of the kneaded sample with that of the reference sample. As shown in FIG. 27, kneading caused increased degree of crystallinity with more defined peak separation. In FIG. 27, the XRPD pattern for the Form I reference sample is shown in black and the XRPD pattern for the kneaded sample is shown in red.

Example 7

Pharmacokinetics of the Compound of Formula I After Intravenous and/or Oral Administration of the Free Base and of Different Salts in Dogs In Example 10, the pharmacokinetics of the compound of Formula I in dogs following single intravenous and oral administration was evaluated and the oral bioavailability of five different salts of the compound of Formula I was compared. The compound of Formula I was administered to dogs as described in Table 12. The doses are expressed in mg of free base.

TABLE 12

Formula I Dosage Forms and Administration.

| Sample | Protocol Ref. | Administration Route | Formulation | Dose |
|---|---|---|---|---|
| Hydrochloride Salt | A | p.o | Capsule | 120 mg/dog |
| Malate salt | A | p.o | Capsule | 120 mg/dog |
| Tartrate Salt | A | p.o | Capsule | 120 mg/dog |
| Free Base | A | p.o | Capsule | 120 mg/dog |
| Free Base | B | p.o | Capsule | 70 mg/dog |
| Tartrate | B | p.o | Capsule | 70 mg/dog |
| Mesylate | B | p.o | Capsule | 70 mg/dog |

Test Animals

The experiments were performed in 15 male dogs (body-weight 11-18 kg) from RCC Ltd., Biotechnology and Animal Breeding Division, Wolferstrasse 4, CH-4414, Fullinsdorf, Switzerland. The animals were housed under standard laboratory conditions throughout the study period. They were fasted overnight before drug administration and had free access to water and food during the experiment.

Sample Collection

For the pharmacokinetic studies, 1 mL blood samples were collected from the cephalic vein of the dogs via catheter at 15, 30 min and at 1, 2, 3, 4, 6, 8, 24, 32, 48, 56, 72, 80, 96, and 100 (or 104) hours following oral dosing. After intravenous administration, blood samples were collected at 5, 15, 30 min and 1, 2, 3, 4, 6, 8, 24, 32, 48, 56, 75, 102, 120, 128, 144, 152, 168, 176, 192, and 200 hours. Collection tubes contained EDTA/NaF as anticoagulant and stabilizer. After centrifugation, plasma was removed and stored deep frozen at approximately −20° C. until analysis using a specific LC-MS method.

Analytical Methods

Protocol A

Aliquots of 40 μL plasma were mixed with 50 μL buffer at pH 5, 50 μL internal standard of Formula I (1 μg/mL in 1-chlorobutane) and 250 μL butylacetate and then shaken for 10 min. After centrifugation, 200 μL of the supernatant were evaporated to dryness at 45° C. under a stream of nitrogen. The residue was reconstituted with 200 μL acetonitrile/1% formic acid in water (30/70, v/v). Aliquots of 30 μL were injected onto the analytical column (Waters, Symmetry C8, 2.1×150 mm, 5 m).

Separation occurred by gradient elution using a solvent A (acetonitrile) and solvent B (1% formic acid in water). The flow rate was 0.3 mL/min and the gradient elution was:

| Time (min) | Mobile Phase A (%) | Mobile Phase B (%) |
|---|---|---|
| 0 | 30 | 70 |
| 5 | 60 | 40 |
| 9 | 60 | 40 |
| 10 | 30 | 70 |

The sample passed to the ion-spray interface of the single quadrupole mass spectrometer. Selected ion monitoring mode (SIM) was used for mass spectrometric detection. Quantification was based on peak area ratios and calibration curve established between 2 and 5000 ng/mL.

Protocol B

To a 100 μL sample aliquot were added 200 μL of a mixture of acetonitrile/ethanol containing the deuterated internal standard, to precipitate plasma proteins. After vortex mixing and centrifugation, aliquots of the supernatants were transferred to 96-deel-well plates and injected for analysis (5 μL). Following enrichment and cleanup on the trapping column, the analyte was eluted and separated by gradient elution on a 2.1*30 mm analytical column (XTerra MS C18). The effluent from the analytical column was passed to the turbo ion spray vie a divert valve.

Calibration standards were prepared in dog plasma. The calibration range was from 10-5000 ng/mL. In each analytical series, a set of calibration standards was worked up and run with the unknowns. Calibration was then performed by computing a weighted ($1/X^2$) least-squares linear regression line of the measured peak area ratios (Y) (analyte to internal standard) versus the spiked concentrations (X). The drug concentrations of the unknown samples were then calculated from this regression line (UNICHROM). The performance of the analytical procedure during sample analysis was monitored. With each analytical series, quality control (QC) samples in dog plasma, spiked with known amounts of the analyte, were run together with the study samples.

Not all samples were collected at the times specified in the protocols. This did not compromise the outcomes of the study, as the actual sampling times were recorded and were used for the pharmacokinetic analysis.

Data Processing

Data acquisition and integration was performed using software packages Sample Control and MacQuan from PE Sciex. MacQuan was additionally used to generate an ASCII file, containing the relevant sample information of the actual analytical series to be used for the calculation of the regression line and of the drug concentrations of the unknowns. This file was transferred to the VAX based software package Unichrom 1.5 for further concentration calculations. The calculated analytical results were then stored in the database Kinlims.

Kinetic Analysis

The pharmacokinetic parameters were estimated by non-compartmental analysis, using the pharmacokinetic evaluation program WinNOnlin [1]. AUC(0-inf) was calculated applying the linear trapezoidal rule and extrapolation to infinity using the apparent elimination rate constant λz and the calculated concentration at the last measurable time point. AUClast values were calculated by linear trapezoidal rule from time zero to time of last measureable time point. Cmax, C(t), and Tmax were determined directly from the plasma concentration-time profiles. The apparent terminal half-life ($T_{1/2}$) was derived from the equation: $T_{1/2}=\ln2/\lambda z$. Means of the half-life were calculated by harmonic means. Plasma clearance, CL, was calculated as D/AUC(0-inf.). Volume of distribution, Vz, was calculated as CL/λz. The absolute bioavailability was calculated from plasma concentration data as follows:

$$F(\%) = \frac{AUC(0-\infty)_{p.o.}}{AUC(0-\infty)_{i.v.}} * \frac{D_{i.v.}}{D_{p.o.}} * 100$$

Possible small deviations of the reported mean values from those calculated from non-rounded pharmacokinetic parameters are due to the rounding procedure of individual values.

Assay Performance

The performance of the LC-MS assay was assessed from the analysis of quality control samples, which were measured alongside the unknown samples.

For Protocol A, the average inter-assay precision was 6.3% in the concentration range 2-5000 ng/mL plasma and the corresponding inter-assay inaccuracy averaged 11% for plasma. The quantification limit was set to 4 ng/mL (20% below the lowest calibration point). This was considered to be adequate to reach the objective of the study.

For Protocol B, the average inter-assay precision was 5.1% in the concentration range of 10-5000 ng/mL plasma and the corresponding inter-assay inaccuracy averaged 4.4% for plasma. The quantification limit was set to 10 ng/mL. This was considered to be adequate to reach the objective of the study.

The calculated pharmacokinetic parameters are compiled in Tables 13-14.

TABLE 13

Pharmacokinetics of Formula I Following Single Oral Administration of 120 mg Free Base and Salts to dogs.

| | Formulation | | | | | | | |
|---|---|---|---|---|---|---|---|---|
| | Hydrochloride | | Malate | | Tartrate | | Free Base | |
| Dog No. | | | | | | | | |
| | 6461 | 5563 | 6464 | 6452 | 6482 | 6460 | 2375 | 5547 |
| Dose* (mg/kg) | 8.6 | 8.7 | 7.8 | 8.0 | 10.3 | 10.1 | 8.0 | 7.9 |
| Cmax (ng/mL) | 1110 | 733 | 1430 | 1090 | 1160 | 1970 | 614 | 757 |
| Tmax (h) | 1.0 | 4.0 | 3.0 | 4.0 | 6.0 | 3.0 | 2.0 | 2.0 |
| AUC (0-100 h) (ng·h/mL) | 25900 | 20900 | 40000 | 21600 | 26300 | 45500 | 11000 | 17400 |
| AUC (0-Inf.) (ng·h/mL) | 36400 | 26900 | 58100 | 26300 | 28800 | 55800 | 12700 | 22600 |
| $T_{1/2}$ (h) | 64.0 | 48.2 | 64.4 | 44.0 | 35.0 | 42.6 | 39.5 | 56.3 |
| F (%) | 91.4 | 66.7 | 161 | 71.0 | 60.3 | 119 | 34.3 | 61.7 |
| F** (%) | — | — | 130 | — | — | 115 | — | — |

*Dose expressed in mg of free base
**Calculated with mean AUC(0-102 h) of 11800 ng·h/mL after i.v. application of 3 mg/kg Formula I (n = 3)

TABLE 14

Pharmacokinetics of Formula I Following Single Oral Administration of 70 mg Free Base and Salts to dogs.

| | Formulation | | | | | |
|---|---|---|---|---|---|---|
| | Free Base | | Tartrate | | Mesylate | |
| Dog No. | | | | | | |
| | 6460 | 5455 | 6396 | 6452 | 6392 | 6393 |
| Dose* (mg/kg) | 5.0 | 4.9 | 5.1 | 5.4 | 5.4 | 6.3 |
| Cmax (ng/ml) | 587 | 667 | 1120 | 358 | 320 | 287 |
| Tmax (h) | 6 | 4 | 2 | 3 | 4 | 3 |
| AUC (0-100 h) (ng·h/mL) | 16200 | 12800 | 23400 | 10700 | 6380 | 7550 |
| AUC (0-Inf.) (ng·h/mL) | 19300 | 14500 | 31000 | 12300 | 7150 | 8100 |
| $T_{1/2}$ (h) | 40.4 | 35.7 | 53.1 | 34.8 | 41.2 | 26.7 |
| F (%) | 83.3 | 63.9 | 131 | 49.2 | 28.6 | 27.7 |
| F** (%) | — | — | 117 | — | — | — |

*Dose expressed in mg of free base
**Calculated with mean AUC(0-102 h) of 11800 ng·h/mL after i.v. application of 3 mg/kg Formula I (n = 3)

Oral Administration

The free base of the compound of Formula I and three different salts of Formula I (hydrochloride, malate, and tartrate) were administered orally in a gelatin capsule (120 mg/capsule calculated as free base) to two dogs per salt. In a further experiment, two different salts of the compound of Formula I (tartrate and mesylate) and free base were administered orally in a gelatin capsule (70 mg/capsule calculated as free base) to two dogs per salt.

After oral administration of the compound of Formula I as a free base to two dogs (Protocol A) Cmax values of 614 and 757 ng/mL were achieved at 2 hours following the administration. In these two animals the oral bioavailabilies were 40 and 56%, respectively. In a second experiment (Protocol B), after administration of lower doses of Formula I, Cmax of 587 and 667 ng/mL were achieved between 4 and 6 hours after dosing. The oral bioavailabilies were slightly higher than in the first experiment with oral bioavailability values of 83 and 64% respectively. In the four animals, the apparent terminal half-lives ranged between 36 and 56 hours. For these two experiments, two different batches of the compound of Formula I were used. A difference in particle size might explain the observed differences between both experiments. For the first batch, which was not milled, the particle size was estimated to be about 10 to 20 m, whereas in the second batch which was fine milled the measured particle size was 3-6 m. In addition, these experiments were conducted in different animals (parallel groups) and the difference in bioavailability might also be attributed to inter-individual variability.

After oral administration of the hydrochloride salt to two dogs, Cmax values of 1110 and 733 ng/mL were achieved at 1 and 4 hours after dosing, respectively. The systemic bioavailabilites were at 91 and 67% in both animals. The apparent terminal half-lives (64 and 44 hours, respectively) were similar to those observed in other animals.

Oral administration of the malate salt to two dogs showed Cmax values of 1430 and 1090 ng/mL, which were achieved 3 to 4 hours following dosing. The oral bioavailability values were 161 and 70%, respectively. The one animal with the bioavailability value of 161% showed a flat plasma concentration-time profile, with a terminal half-life of 64 hours. Therefore, the oral bioavailability in this animal might be overestimated by using extrapolated areas under the curve values. With truncated areas under the curves (AUC0-1-104 h), the oral bioavailability of Formula I in this animal was still 130%. The reason for this high value remained unclear.

After oral application of the tartrate salt to four dogs, Cmax values were 1160 and 1970 ng/mL (120 mg dose) and 1120 and 358 ng/mL (70 ng dose). Peak concentrations were achieved between 2 and 6 hours after dosing. The apparent terminal half-lives ranged between 35 and 53 hours and the systemic bioavailabilies ranged between 49 and 131%.

After oral administration of the mesylate salt to 2 dogs, Cmax values were lower than with the base and the different other salts tested. They were 320 and 287 ng/mL and were achieved at 4 and 3 hours after dosing, respectively. The systemic bioavailabilies were 29 and 28%, respectively. The apparent terminal half-lives were 41 hours and 27 hours.

During the course of the experiments, no overt pharmacological or toxicological signs were observed in dogs.

Conclusions

The results indicated an oral bioavailability of Formula I ranging from 34 to 83% following administration of the free base in gelatin capsule form. The results also indicate an oral bioavailability of Formula I ranging from 28 to 160% following oral administration of Formula I in the form of different salts (hydrochloride, malate, tartrate, mesylate) in gelatin capsule form, the lowest bioavailability being observed with the mesylate salt (28%). Based on pharmacokinetic as well as on galenical considerations, the free base was considered as suitable for further development of the compound of Formula I.

Example 8

Pharmacokinetics and Brain Penetration of the Compound of Formula I in Rats

In Example 11, the pharmacokinetics of the compound of Formula I was evaluated following single intravenous, intraperitoneal, and oral administration to rats to compare the oral bioavailability of two different formulations and to measure the brain penetration after intravenous administration.

Dosage Forms and Administration

A solution of the compound of Formula I (4.7 mg/mL) in water and a suspension of the compound of Formula I (5 mg/mL) in SSV (standard suspension vehicle) were prepared. The compound of Formula I (doses expressed as free base) was administered to rats as set forth in Table 15.

TABLE 15

Formula I Dosage Forms and Administration.

| Rat No. | Protocol | Route | Formulation | Dose (mg/kg) |
|---|---|---|---|---|
| NJ418-423/98 | 192/98 Lt | i.p., p.o., i.v. | Solution in water | 9.4* |
| NJ672-679/98 | 193/98 Lt | i.v. | Solution in water | 9.4* |
| NJ97-98/99 | 43/99 Sp | p.o. | Suspension in SSV | 10 |
| NJ99-102/99 | 43/99 Sp | p.o., i.v. | Solution in water | 9.4 |

*Corresponding to 10 mg/kg Formula I

Test Animals

The experiments were performed in 20 male rats (Strain RoRo Fuellinsdorf, body weight 230-290 g) from Biological Research Laboratories, Fuellinsdorf, Switzerland. The animals were housed under standard laboratory conditions throughout the study period. After an acclimatization period of 3 days, the rats were implanted with chronic jugular catheters under pentobarbital anesthesia. After surgery the rats were on recovery for 2 days before dosing. They had free access to water and food during the experiment.

Sample Collection

For the pharmacokinetic studies, 0.4 mL blood samples were collected at different time points, up to 72 hours post-dose, from the jugular vein of the rats via catheter. For the study of brain and CSF penetration, 2 mL blood samples as well as CSF and brain were collected between 0.3 and 2 hours post-dose from one rat at each time point. Collection tubes contained EDTA/NAF as anticoagulant and stabilizer, respectively. After centrifugation, plasma was removed. Plasma, CSF and brain samples were stored deep-frozen at approximately −20° C. until analysis using a specific LC-MS method.

Plasma Sample Preparation

Aliquots of plasma samples of 40 μL were mixed with 50 μL buffer pH 9, 50 μL of a Formula I internal standard (1 μg/mL 1-chlorobutane) and 250 μL butylacetate and then shaken for 10 min. After centrifugation, 200 μL of the supernatant were evaporated to dryness at 45° C. under a stream of nitrogen. The residue was reconstituted with 200 μL acetonitrile/1% formic acid in water (30/70, v/v). An aliquot of 30 μL was injected onto an analytical column (Waters, Symmetry C8, 2.1×150 mm, 5 μm).

Brain and CSF Sample Preparation

The frozen half brain was weighed. After thawing, the tissue was suspended in a 2 mL eppendorf polypropylene tube with 2 volumes of sterile apyrogen and cold NaCl (+4° C.; 0.9% solution) (0.333 g brain/mL NaCl). The tissue was homogenized (ice bath) using a Vibra-Cell ultrasonic processor (Sonics & Material, Inc. Danbury, CT-USA) for 2×10 s (amplitude: 60, energy: 25). An aliquot of the resulting brain homogenate (40 μL) was used for extraction as described for plasma. 50 μL CSF with 50 μL plasma were used for extraction as described under plasma sample preparation. Separation occurred by gradient elution using a solvent A (acetonitrile) and a solvent B (1% formic acid in water). The flow rate was 0.3 mL/min and the gradient elution was:

| Time (min) | Mobile Phase A (%) | Mobile Phase B (%) |
|---|---|---|
| 0 | 30 | 70 |
| 5 | 60 | 40 |
| 9 | 60 | 40 |
| 10 | 30 | 70 |

The sample passed to the ion-spray interface of the single quadrupole mass spectrometer. Selected ion monitoring mode (SIM) was used for mass spectrometric detection. Quantification was based on peak area ratios and calibration curve established by weighted $(1/x^2)$ linear regression. The calibration curve was established between 5 and 5000 ng/mL using dog plasma as matrix. Data acquisition and integration of SIM chromatograms were performed using MacQuan (version 1.6) from Perkin-Elmer Sciex.

Kinetic Analysis

The pharmacokinetic parameters were estimated by non-compartmental analysis, using the pharmacokinetic evaluation program WinNOnlin [1]. AUC(0-inf) was calculated applying the linear trapezoidal rule and extrapolation to infinity using the apparent elimination rate constant λz and the calculated concentration at the last measurable time point. AUClast values were calculated by linear trapezoidal rule from time zero to time of last measureable time point. Cmax, C(t), and Tmax were determined directly from the plasma concentration-time profiles. The apparent terminal half-life ($T_{1/2}$) was derived from the equation: $T_{1/2}=\ln2/\lambda z$. Means of the half-life were calculated by harmonic means. Plasma clearance, CL, was calculated as D/AUC(0-inf.). Volume of distribution, Vz, was calculated as CL/$\lambda$z. The absolute bioavailability was calculated from plasma concentration data as follows:

$$F(\%) = \frac{AUC(0-\infty)_{p.o.}}{AUC(0-\infty)_{i.v.}} * \frac{D_{i.v.}}{D_{p.o.}} * 100$$

Possible small deviations of the reported mean values from those calculated from non-rounded pharmacokinetic parameters are due to the rounding procedure of individual values. Apart from calculating mean values, no formal statistical analysis was performed because of the low number of animals.

Assay Performance

The performance of the LC-MS assay was assessed from the analysis of control samples which were measured alongside unknown samples. The average inter-assay precision was 7.3% for rat plasma and 1.9% for dog plasma in the concentration range of 5-2000 ng/mL. The corresponding inter-assay inaccuracy averaged 2.7% for rat plasma, 5.3% for dog plasma and 5.0% for brain samples. The quantification limit was set to 4 ng/mL (200% below the lowest calibration point). This was considered to be adequate to reach the objective of the study.

Plasma Concentrations of the Compound of Formula I and Derived Pharmacokinetic Parameters The plasma concentration-time curves of the compound of Formula I following intravenous or oral administration to rats are shown in Tables 16-17.

The calculated pharmacokinetic parameters are compiled in Tables 16-17.

TABLE 16

Pharmacokinetics of Formula I Following Single Oral, Intraperitoneal and Intravenous Administration of Formula I (Free Base) in Water (9.4 mg/kg Free Base) to Rats.

| | Formulation Admin. Route | | | | | |
|---|---|---|---|---|---|---|
| | Formula I (water, p.o) | | Formula I (water, i.p.) | | Formula I (water, i.v.) | |
| | | | Rat No. | | | |
| | NJ418 | NJ419 | NJ420 | NJ421 | NJ422 | NJ423 |
| Cmax (ng/mL) | 991 | 682 | 1610 | 1730 | — | — |
| Tmax (h) | 2 | 4 | 0.25 | 0.25 | — | — |
| AUC (0-24 h) (ng · h/mL) | 15000 | 12600 | 26800 | 19900 | 29200 | 24400 |
| CL* (mL/min/kg) | — | — | — | — | 5.38 | 6.44 |
| $T_{1/2}$ (h) | 17.7 | 18.9 | 106 | 28.1 | 35.9 | 12.5 |
| Vz* (L/kg) | — | — | — | — | 16.7 | 6.97 |
| F (%) | 56.0 | 47.0 | 100 | 74.3 | — | — |

*Calculated with AUC (0-24 h)

TABLE 17

Pharmacokinetics of Formula I Following Single Oral Administration of Formula I (Hydrochloride Salt) in SSV, and Single Oral and Intravenous Administration of Formula I (Hydrochloride Salt) (9.3 mg/kg Free Base) in Water to Rats.

| | Formulation Admin. Route | | | | | |
|---|---|---|---|---|---|---|
| | Formula I (HCl salt) (water, p.o) | | Formula I (HCl salt) (water, i.p.) | | Formula I (HCl salt) (water, i.v.) | |
| | | | Rat No. | | | |
| | NJ97 | NJ98 | NJ99 | NJ100 | NJ101 | NJ102 |
| Cmax (ng/ml) | 616 | 796 | 933 | 1060 | — | — |
| Tmax (h) | 2.2 | 4.0 | 6.3 | 4.0 | — | — |
| AUC (0-48 h) (ng · h/mL) | 12000 | 15200 | 26200 | 20100 | 31700 | 21400 |
| AUC (0-Inf. h) (ng · h/mL) | 12800 | 15800 | 37900 | 34000 | 49300** | 32300** |
| CL* (mL/min/kg) | — | — | — | — | 4.96 | 7.35 |
| $T_{1/2}$ (h) | 11.6 | 10.2 | 26.5 | 27.1 | 25.5*** | 18.2*** |
| Vz* (L/kg) | — | — | — | — | 11.0 | 11.5 |
| F (%) | 42.4 | 53.7 | 98.6 | 75.7 | — | — |

*Calculated with AUC (0-24 h);

**Calculated with AUC (0-72 h);

***Without 72 h concentration

Intravenous Administration

A solution of Formula I (hydrochloride salt) was administered intravenously at a dose of 9.4 mg/kg to 2 male rats in two subsequent experiments. In both studies, blood samples were obtained at 0.083, 0.25, 0.5, 1, 2, 4, 6, 8, and 24 h after intravenous application and in addition at 48 and 72 h in the study.

Following intravenous application, the plasma concentrations showed a short distribution phase followed by a slow decline with a mean apparent terminal half-life of 19.8 h (range 12.5 to 35.9 h, n=4). This long elimination half-life is in line with a low systemic clearance of the test compound (5 to 7 mL/min/kg).

The volume of distribution of Formula I (12 L/kg), much higher than the total body water space in rats, suggested a high extravascular distribution. These data were confirmed during a pilot whole body autoradiography study in rats, which showed an extensive distribution of the labeled compound and/or metabolites as well as a very slow elimination from the body.

In the experiment, the plasma concentration values measured at 72 h following dosing were excluded from the evaluation. Plasma concentrations at 72 h were 4 times higher than those at 48 h. No explanation could be found so far for this observation. Due to this irregular pharmacokinetic behavior with rising plasma concentrations, clearance and volume of distribution were calculated with an AUC from 0 to 24 h for 2 rats and from 0 to 48 h for 2 other animals.

During the course of the studies, no overt pharmacological or toxicological signs were observed in the rats.

Intraperitoneal and Oral Administration to Rats

Two different formulations were administered to rats: (1) a solution of Formula I (hydrochloride salt) was administered intraperitoneally to 2 male rats or orally (gavage) to 4 male rats at a dose of 9.4 mg/kg; and (2) a suspension of Formula I (free base) in SSV (standard suspension vehicle) was administered orally at a dose of 10 mg/kg to 2 male rats.

Blood samples were obtained at 0.25, 0.5, 1, 1.5, 2, 4, 6, 8, and 24 h after administration and in addition at 48 and 72 h.

After intraperitoneal application of the solution, the bioavailability of Formula I was 100 and 74% in the 2 rats. Peak concentrations were reached rapidly, within 0.25 h following dosing. The test compound had an apparent elimination half-life of 106 and 28.1 h, respectively, in the 2 animals.

After oral application of a solution of Formula I (hydrochloride salt) in water to 4 rats, Cmax values ranged from 682 to 1060 ng/mL and were achieved between 2 and 6 hours after dosing. The mean (±SD) apparent terminal half-life of 13.6 h (±4.9 h) is consistent with the mean values found after i.v. administration (19.8 h±10 h). The oral bioavailability ranged from 47 to 98.6% calculated with AUC 0-24 h for protocol 192/98Lt and with AUC 0-48 h for protocol 43/99Sp.

Oral application of a suspension of Formula I (hydrochloride salt) in SSV was compared to oral application of Formula I (hydrochloride salt) in water. After application of free base, maximum plasma concentrations were 616 and 796 ng/mL and were achieved at 2.2 and 4 h, respectively, after dosing. They were lower than peak concentrations reached with the solution of Formula I (hydrochloride salt). The bioavailability of this oral suspension ranged from 42 to 54% (calculated with AUC 0-48 h).

At 72 h post-dose, plasma levels were significantly higher than at 48 h. With the suspension of Formula I (hydrochloride salt) in SSV, the increase was approximately 5-fold. With the solution of Formula I (hydrochloride salt) in water, the increase was very small. The reasons for these findings is unknown.

During the course of the studies, no overt pharmacological or toxicological signs were observed in the rats.

Brain Concentrations

Brains were taken at approximately 0.25, 0.5, 1 and 2 h after intravenous administration of Formula I into the tail vein of 8 rats (2 rats per time point). For all time points, the concentrations were higher in the brain than in the plasma, with ratios of brain homogenate/plasma concentrations of 2.4 to 4.9. The CSF was taken at the same time points and analyzed but the concentrations were low (4.9 to 16 ng/mL or below 4 ng/mL), possibly due to the high plasma protein binding. This result was confirmed by the determination of the binding of Formula I to rat plasma proteins which was 99.8%.

Conclusions

The pharmacokinetics of Formula I was assessed in the rat. The results indicated a long terminal half life of Formula I (19.5 h), in line with a low systemic clearance of the compound in rats (6 mL/min/kg). The results also indicate a high volume of distribution (12 L/kg) indicating a pronounced extravascular distribution of the compound. A penetration of the compound of Formula I into the brain was also observed, as indicated by brain/plasma ratios from 2.4 to 4.9 within 2 h following i.v. administration. The results also indicated an oral bioavailability of Formula I (hydrochloride salt) administered in water ranged from 47 to 100% (n=4). The bioavailability of Formula I (free base) in SSV was 42 and 54%. The free base was considered as suitable for further development of the compound of Formula I.

Figure 11:
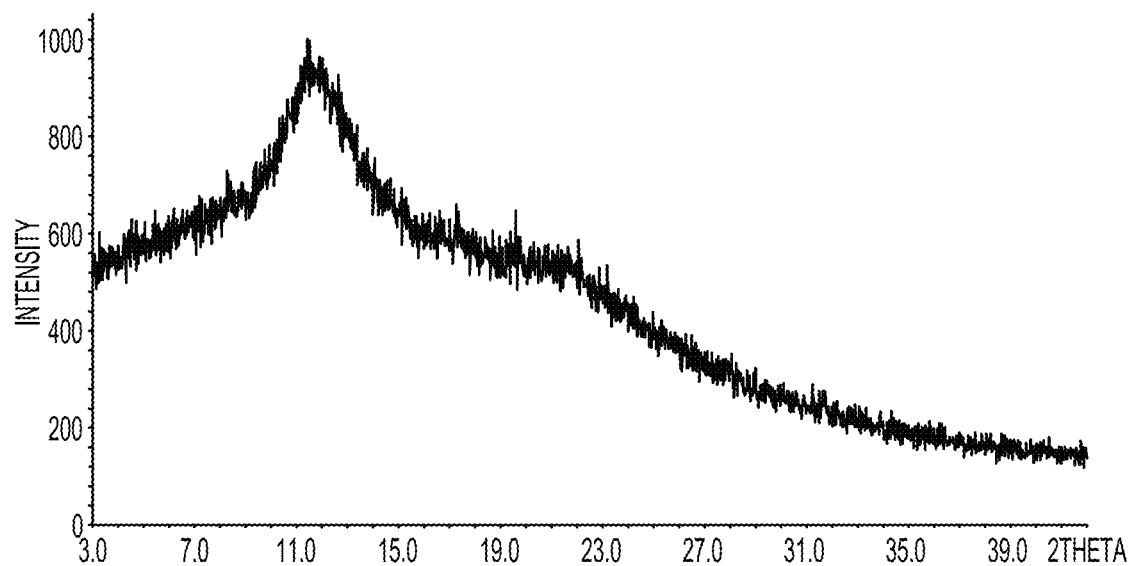
FIG. 11 shows an XRPD pattern for amorphous Formula I.

What is claimed is:

1. Amorphous 2-(3,5-bis(trifluoromethyl)phenyl)-N,2-dimethyl-N-(6-(4-methylpiperazin-1-yl)-4-(o-tolyl)pyridin-3-yl)propenamide having an XRPD pattern substantially as depicted in FIG. 11.

Figure 12:
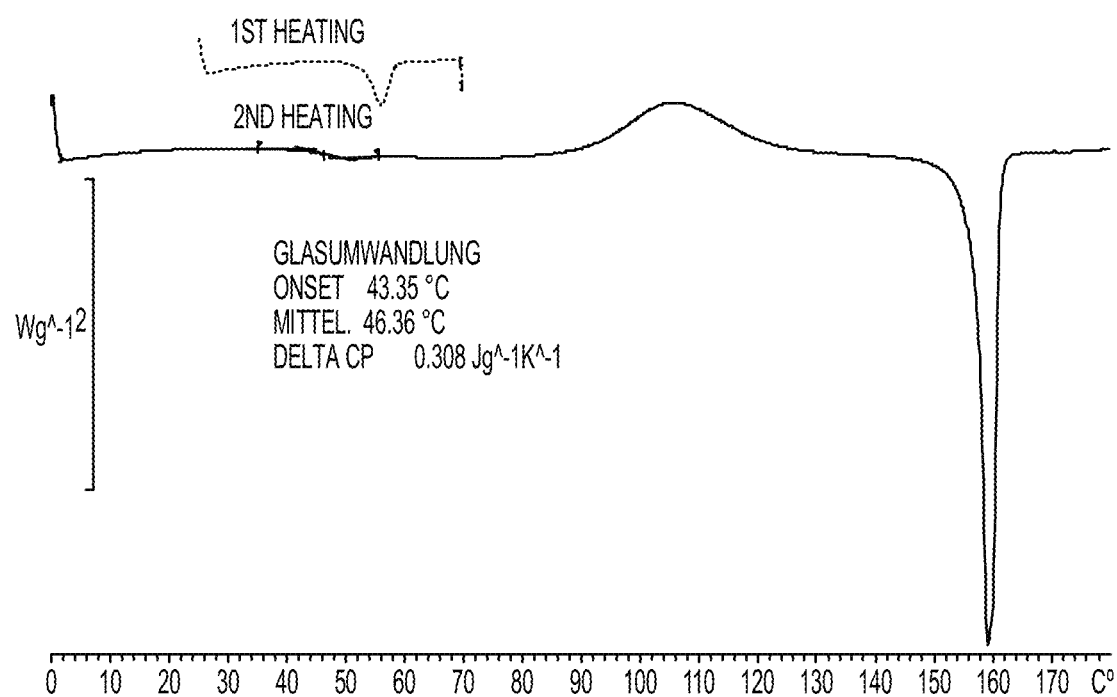
FIG. 12 shows the results of a DSC experiment for amorphous Formula I.

2. The amorphous 2-(3,5-bis(trifluoromethyl)phenyl)-N,2-dimethyl-N-(6-(4-methylpiperazin-1-yl)-4-(o-tolyl)pyridin-3-yl)propenamide of claim 1 having a DSC thermogram substantially as depicted in FIG. 12.

3. The amorphous 2-(3,5-bis(trifluoromethyl)phenyl)-N,2-dimethyl-N-(6-(4-methylpiperazin-1-yl)-4-(o-tolyl)pyridin-3-yl)propenamide of claim 1 having a TGA thermogram substantially as depicted in FIG. 13.

4. The amorphous 2-(3,5-bis(trifluoromethyl)phenyl)-N,2-dimethyl-N-(6-(4-methylpiperazin-1-yl)-4-(o-tolyl)pyridin-3-yl)propenamide of claim 1 having a DVS moisture absorption/desorption pattern substantially as depicted in FIG. 14.

5. Amorphous 2-(3,5-bis(trifluoromethyl)phenyl)-N,2-dimethyl-N-(6-(4-methylpiperazin-1-yl)-4-(o-tolyl)pyridin-3-yl)propenamide having an IR spectrum substantially as depicted in FIG. 15.

6. Amorphous 2-(3,5-bis(trifluoromethyl)phenyl)-N,2-dimethyl-N-(6-(4-methylpiperazin-1-yl)-4-(o-tolyl)pyridin-3-yl)propenamide having an NMR spectrum substantially as depicted in FIG. 16.

* * * * *